US008247553B2

(12) United States Patent
Clark et al.

(10) Patent No.: US 8,247,553 B2
(45) Date of Patent: Aug. 21, 2012

(54) PROCESS OF MAKING ALUMINUM ALKYLS

(75) Inventors: Thomas P. Clark, Sanford, MI (US);
Francis J. Timmers, Midland, MI (US);
Kevin A. Frazier, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 361 days.

(21) Appl. No.: 12/699,260

(22) Filed: Feb. 3, 2010

(65) Prior Publication Data
US 2010/0204500 A1    Aug. 12, 2010

Related U.S. Application Data

(60) Provisional application No. 61/150,424, filed on Feb. 6, 2009.

(51) Int. Cl.
C07F 15/00    (2006.01)
C07F 5/06    (2006.01)
B01J 31/00    (2006.01)
(52) U.S. Cl. .......................................... 546/2; 556/190
(58) Field of Classification Search ....... 546/2; 556/190
See application file for complete search history.

(56) References Cited

U.S. PATENT DOCUMENTS
2,959,607 A    11/1960    Werber et al.
3,391,219 A    7/1968    Davis et al.
5,124,465 A    6/1992    Allen et al.

FOREIGN PATENT DOCUMENTS
WO    2006005762    1/2006
WO    2008112133    9/2008

OTHER PUBLICATIONS

Gibson et al., Dalton Transactions, pp. 2824-2830 (2003).*
Bianchini et al., "Selective Oligomerization of Ethylene to Linear α-Olefins by Tetrahedral Cobalt(II) Complexes with 6-(Organyl)-2-(imino)pyridyl Ligands: Influence of the Heteroatom in the Organyl Group on the Catalytic Activity", Organometallics, 2003; pp. 2545-2547, vol. 22, American Chemical Society.
Bianchini et al., "Oligomerisation of Ethylene to Linear α-Olefins by Tetrahedral Cobalt(II) Precursors Stabilised by benzo[b]thiopen-2-yl-substituted (imino)pyridine ligands", Journal of Organometallic Chemistry, 2003, pp. 1356-1361, vol. 689, No. 8.
Davies et al., "Use of Suzuki cross-coupling as a route to 2-phenoxy-6-iminopyridines and chiral 2-phenoxy-6-(methanamino)pyridines", Tetrahedron, 2008, pp. 9857-9864, vol. 64, Elsevier Ltd.
Irrgang et al., "Sterically Demanding Iminopyridine Ligands", European Journal of Inorganic Chemistry, 2007, pp. 4221-4228.

* cited by examiner

Primary Examiner — Porfirio Nazario Gonzalez

(57) ABSTRACT

The present invention generally relates to a new process of making a trialkyl aluminum compound in which at least one alkyl group is a primary alkyl derived from an internal olefin or alpha-olefin. The process employs an isomerization/hydroalumination catalyst.

19 Claims, 1 Drawing Sheet

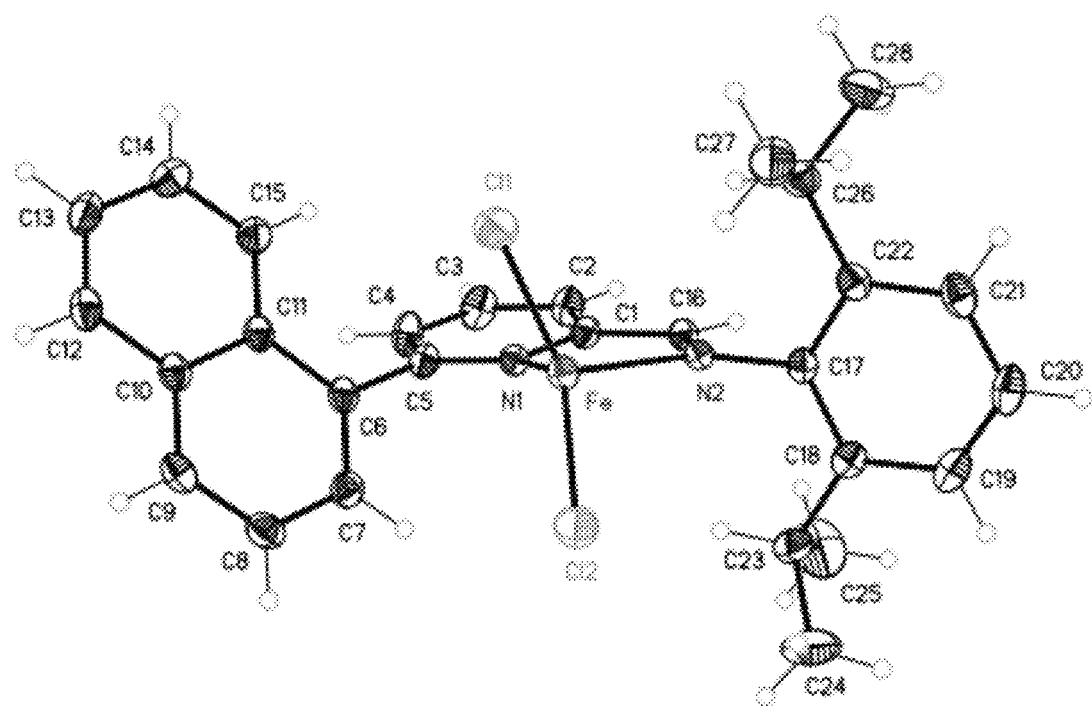

PROCESS OF MAKING ALUMINUM ALKYLS

CROSS-REFERENCE TO RELATED APPLICATION(S)

This application claims benefit from U.S. Provisional Patent Application No. 61/150,424, filed Feb. 6, 2009, the entire contents of which are incorporated herein by reference.

The present invention generally relates to a new process of making a trialkyl aluminum compound in which at least one alkyl group is a primary alkyl derived from an internal olefin or alpha-olefin. The process employs an isomerization/hydroalumination catalyst.

BACKGROUND OF THE INVENTION

A commercially important preparation of an alpha-olefin (also known as α-olefin and 1-olefin) product involves a step of reacting an internal olefin (i.e., a carbon chain comprising a functional group motif, C—C=C—C) with an aluminum alkyl and an isomerization catalyst to form a trialkyl aluminum compound. The trialkyl aluminum compound comprises three alkyl groups, at least one of which is a primary alkyl derived from the internal olefin. (Here a primary alkyl refers to a carbon chain comprising a functional group motif, —$CH_2$—C—C—C wherein the $CH_2$ carbon is bonded to the aluminum). In another step, the process allows the trialkyl aluminum compound to react with a sacrificial 1-olefin and a displacement catalyst so as to displace the primary alkyl derived from the internal olefin from the trialkyl aluminum compound and thereby form the alpha-olefin product. The isomerization and displacement catalysts may be the same or different and typically comprise nickel. Alternatively, the displacement reaction may be run without catalyst at elevated temperature with short residence time in the presence of excess of a sacrificial 1-olefin to generate the alpha-olefin.

The trialkyl aluminum compounds having at least one primary alkyl may also be prepared directly from the alpha-olefin. As such, the trialkyl aluminum compounds are also useful intermediates in preparations of primary alcohols and certain other functionalized derivatives of the primary alkyl such as hydroformylated derivatives.

U.S. Pat. No. 2,959,607 mentions a method of forming a trialkyl aluminum compound containing at least one 1-octyl group by reacting oct-2-ene and aluminum tris(1-methylpropyl) in the presence of cobalt chloride catalyst. Also mentioned is converting the trialkyl aluminum compound to 1-octanol by oxidation and hydrolysis.

U.S. Pat. No. 5,124,465 mentions a method of preparing a linear 1-olefin (i.e., linear alpha-olefin) from an internal olefin via a trialkyl aluminum compound in which at least one alkyl group is a primary alkyl derived from the internal olefin. Also mentioned are certain cobalt salts or complexes.

PCT International Patent Application Publication Number WO 2006/005762 A1 mentions dimerizing linear alpha-olefins to give an internal olefin dimer, and converting the internal olefin dimer to a 1-olefin using a process analogous to that referenced above. Also mentioned are certain cobalt salts or complexes such as, for example, 2-[1-(2-tertiary-butylphenylimino)ethyl]-6-[1-(4-eicosanoxy-3,5-diphenylphenylimino)ethyl]pyridine cobalt[II] chloride complex of the following formula:

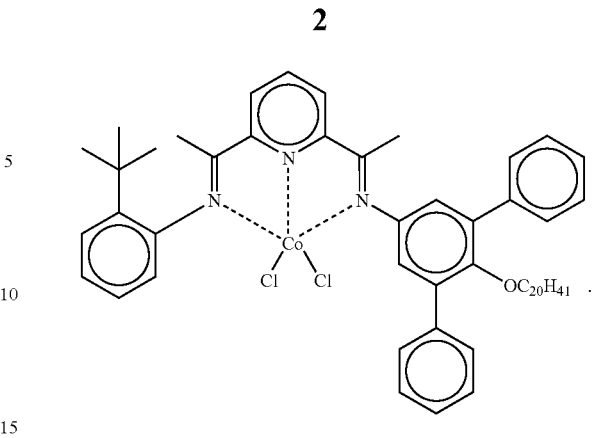

Bianchini C., et al., *Selective Oligomerization of Ethylene to Linear α-Olefins by Tetrahedral Cobalt(II) Complexes with 6-(Organyl)-2-(imino)pyridyl Ligands: Influence of the Heteroatom in the Organyl Group on the Catalytic Activity*, Organometallics, 2003; 22:2545-2547, mention catalysts formed from certain pyridinimine ligands bearing appropriate substituents in the 6-position of the pyridine ring, cobalt dichloride ($CoCl_2$), and methylaluminoxane (MAO). The catalysts are useful for oligomerization of ethylene ($CH_2$=$CH_2$) to give alpha-olefins. Also mentioned are certain cobalt salts or complexes such as, for example, a cobalt [II] chloride complex of the following formula:

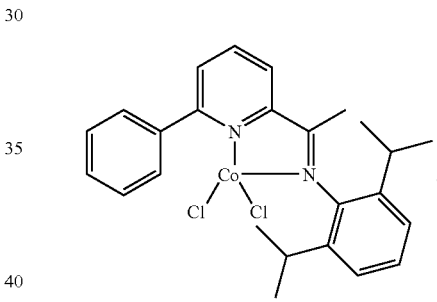

PCT International Patent Application Publication Number WO 2008/112133 A2 mentions preparation of certain 2-imine-substituted pyridines as intermediates in the preparation of certain 2-aminomethyl-substituted pyridines as tridentate ligands to hafnium useful in preparing certain diblock copolymers, triblock copolymers, and multiblock copolymers from propylene and one or more copolymerizable comonomers other than propylene.

Chemical industry desires new processes of making trialkyl aluminum compounds in which at least one alkyl group is a primary alkyl derived from an internal olefin or alpha-olefin. Preferably, the new processes would employ isomerization/hydroalumination catalysts having improved stabilities and higher turnovers compared to those of pertinent commercial nickel catalysts such as, for example, bis(1,5-cyclooctadiene)nickel(0) ($Ni(COD)_2$).

SUMMARY OF THE INVENTION

In a first embodiment, the present invention is a process of preparing a trialkyl aluminum compound, the process comprising a step of contacting together ingredients comprising ingredients (a), (b), and (c):

(a) a precursor trialkyl aluminum of formula (A):

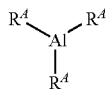
(A)

wherein of the three $R^A$ in formula (A), two $R^A$ independently are $(C_1-C_{40})$alkyl and one $R^A$ independently is $(C_2-C_{40})$alkyl;
(b) an internal olefin of formula (B):

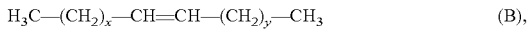
$H_3C$—$(CH_2)_x$—$CH$=$CH$—$(CH_2)_y$—$CH_3$ (B), wherein each of x and y independently is an integer of from 0 to 50, or
an alpha-olefin of formula (E):

$CH_2$=$CH_2$—$(CH_2)_z CH_3$ (E), wherein z is an integer equal to the sum of 1+x+y; or a mixture comprising the internal olefin of formula (B) and the alpha-olefin of formula (E); and
(c) a catalytic amount of an isomerization/hydroalumination catalyst of formula (I):

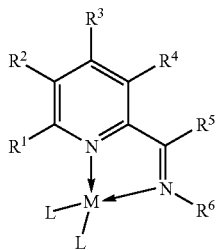
(I)

wherein:
Each of $R^1$ and $R^6$ independently is a $(C_1-C_{40})$hydrocarbyl;
Each of $R^2$, $R^3$, $R^4$, and $R^5$, independently is a hydrogen atom or $(C_1-C_{40})$hydrocarbyl;
Each L independently is a halo, hydrogen atom, $(C_1-C_{40})$hydrocarbyl, $(C_1-C_{40})$heterohydrocarbyl, $(C_1-C_{40})$hydrocarbylC(O)N(H)—, $(C_1-C_{40})$hydrocarbylC(O)N($(C_1-C_{20})$hydrocarbyl)-, $(C_1-C_{40})$hydrocarbylC(O)O—, $R^KR^LN$—, $R^LO$—, $R^LS$—, or $R^KR^LP$—, wherein each $R^K$ and $R^L$ independently is a hydrogen atom, $(C_1-C_{40})$hydrocarbyl, $[(C_1-C_{10})$hydrocarbyl$]_3$Si, $[(C_1-C_{10})$hydrocarbyl$]_3$Si$(C_1-C_{10})$hydrocarbyl, or $(C_1-C_{40})$heterohydrocarbyl, or $R^K$ and $R^L$ are taken together to form a $(C_2-C_{40})$hydrocarbylene or $(C_1-C_{40})$heterohydrocarbylene, wherein each L independently is a mono anionic moiety that is bonded to M; and
Each M independently is a metal that is iron, cobalt, nickel, copper, or zinc, the metal being in a formal oxidation state of +2;
Each of the aforementioned $(C_1-C_{40})$alkyl, $(C_1-C_{10})$hydrocarbyl, $(C_1-C_{20})$hydrocarbyl, $(C_1-C_{40})$hydrocarbyl, $(C_1-C_{40})$heterohydrocarbyl, $(C_2-C_{40})$hydrocarbylene, and $(C_1-C_{40})$heterohydrocarbylene independently is the same as or different than another (e.g., each $(C_1-C_{40})$alkyl is the same as or different than another $(C_1-C_{40})$alkyl, and so on) and independently is unsubstituted or substituted with one or more substituents $R^S$; and
Each $R^S$ independently is halo, polyfluoro, perfluoro, unsubstituted $(C_1-C_{18})$hydrocarbyl, $F_3C$—, $FCH_2O$—, $F_2HCO$—, $F_3CO$—, oxo (i.e., =O), $R_3Si$—, RO—, RS—, RS(O)—, RS(O)$_2$—, $R_2P$—, $R_2N$—, $R_2C$=N—, NC—, RC(O)O—, ROC(O)—, RC(O)N(R)—, or $R_2NC(O)$—, wherein each R independently is an unsubstituted $(C_1-C_{18})$hydrocarbyl;
wherein the contacting step is performed under (trialkyl aluminum compound)-forming conditions (described later) and prepares a trialkyl aluminum compound of formula (D):

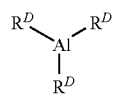
(D)

wherein at least one $R^D$ is a primary alkyl group derived from the internal olefin of formula (B) or derived from the alpha-olefin of formula (E), and any remaining $R^D$ independently are $(C_1-C_{40})$alkyl.
Preferably, M is iron or cobalt, more preferably cobalt. Preferably, the primary alkyl group is of formula —$(CH_2)_t CH_3$, wherein t is an integer equal to the sum of 3+x+y, which also equals the sum of 2+z.

In a second embodiment, the present invention is the isomerization/hydroalumination catalyst of formula (I), wherein $R^1$ to $R^6$, and L independently are as defined for formula (I) above in the first embodiment and M independently is a metal that is iron, nickel, copper, or zinc, the metal being in a formal oxidation state of +2. Preferably, M is iron.

In a third embodiment, the present invention is an isomerization/hydroalumination catalyst of formula (I) having the formula (II):

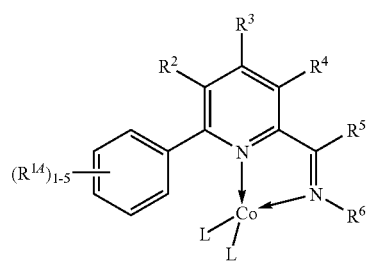
(II)

wherein $R^2$ to $R^6$, and L independently are as defined above for formula (I) in the first embodiment; Co is cobalt in a formal oxidation state of +2; and each of the from 1 to 5 $R^{14}$ independently is a $(C_1-C_{40})$alkyl that is unsubstituted or substituted with one or more substituents $R^S$, wherein each $R^S$ independently is as defined above for formula (I) of the first embodiment, or any two adjacent $R^{14}$ are taken together to form diradical of formula: —C(H)=C(H)—C(H)=C(H)— and the remainder of $R^{14}$ are hydrogen atoms.

The trialkyl aluminum compound of formula (D) is useful for making alpha-olefins (e.g., the alpha-olefin of formula (E)) and functionalized derivatives of the alpha-olefin of formula (E). Such functionalized derivatives include, but are not limited to, primary alcohols of formula (F): HO—$(CH_2)_t CH_3$ (F), wherein t is as defined above. The alpha-olefins of formula (E) are useful for, among other things, preparing polyolefins, including copolymers of the alpha-olefins with ethylene. The polyolefins are prepared as, and are useful in, for example, coatings, lubricants, films, fibers, and molded and extruded articles. Alcohols of formula (F) are useful as, among other things, ingredients in lubricants, ointments, and shampoos and as intermediates for preparing carboxylic esters useful in perfumery and flavors.

Additional non-limiting embodiments are described below.

BRIEF DESCRIPTION OF THE DRAWINGS

FIG. 1 shows an Oak Ridge Thermal Ellipsoid Plot (ORTEP) depiction of a single crystal structure derived by x-ray analysis of isomerization/hydroalumination catalyst (1) of Example (1).

DETAILED DESCRIPTION OF THE INVENTION

As used herein, "a," "an," "the," "at least one," and "one or more" are used interchangeably. In any embodiment described herein, the open-ended (non-excluding) terms "comprising," "comprises," and the like (which are synonymous with "including," "having," and "characterized by") may be replaced by the respective partially closed (partially excluding) phrases "consisting essentially of," consists essentially of," and the like or the respective closed (excluding) phrases "consisting of," "consists of," and the like. The term "or" used in a listing of members, unless stated otherwise, refers to the listed members individually as well as in any combination.

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, headings (e.g., "Definitions") are used for convenience and are not meant, and should not be used, to limit scope of the present disclosure in any way.

In the present application, any lower limit of a range of numbers, or any preferred lower limit of the range, may be combined with any upper limit of the range, or any preferred upper limit of the range, to define a preferred embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

In an event where there is a conflict between a unit value that is recited without parentheses, e.g., 2 inches, and a corresponding unit value that is parenthetically recited, e.g., (5 centimeters), the unit value recited without parentheses controls.

DEFINITIONS

When used to describe a chemical group (e.g., $(C_1-C_{40})$ alkyl), the parenthetical expression of the form "$(C_x-C_y)$," means the chemical group comprises from a number x carbon atoms to a number y carbon atoms, wherein each x and y independently is an integer as described for the chemical group. Thus, for example, an unsubstituted $(C_1-C_{40})$alkyl contains from 1 to 40 carbon atoms. When one or more substituents on the chemical group contain one or more carbon atoms, the substituted $(C_x-C_y)$ chemical group may comprise more than y total carbon atoms; i.e., the total number of carbon atoms of the substituted $(C_x-C_y)$ chemical group is equal to y plus the number of carbon atoms of each of the substituent(s).

In some embodiments, each of the $R^{1A}$, $R^1$ to $R^6$ and L groups of the isomerization/hydroalumination catalyst of formula (I) is unsubstituted, that is, can be defined without use of a substituent $R^S$. In other embodiments, at least one of the $R^{1A}$, $R^1$ to $R^6$ and L groups of the isomerization/hydroalumination catalyst of formula (I) independently contain one or more of the substituents $R^S$. Preferably there are not more than a total of 20 $R^S$, more preferably not more than a total of 10 $R^S$, and still more preferably not more than a total of 5 $R^S$ in the isomerization/hydroalumination catalyst of formula (I). Where the invention compound contains two or more substituents $R^S$, each $R^S$ independently is bonded to a same or different substituted chemical group.

In some embodiments, at least one $R^S$ is polyfluoro or perfluoro. For present purposes "polyfluoro" and "perfluoro" each count as one $R^S$ substituent. The term "poly" as in "polyfluoro" means that two or more H, but not all H, bonded to carbon atoms of a corresponding unsubstituted chemical group are replaced by a fluoro in the substituted chemical group. The term "per" as in "perfluoro" means each H bonded to carbon atoms of a corresponding unsubstituted chemical group is replaced by a fluoro in the substituted chemical group.

As used herein, the term "$(C_1-C_{40})$hydrocarbyl" means a hydrocarbon radical of from 1 to 40 carbon atoms and the term "$(C_1-C_{40})$hydrocarbylene" means a hydrocarbon diradical of from 1 to 40 carbon atoms, wherein each hydrocarbon radical and diradical independently is aromatic or non-aromatic, saturated or unsaturated, straight chain or branched chain, cyclic (including mono- and poly-cyclic, fused and non-fused polycyclic) or acyclic, or a combination of two or more thereof; and each hydrocarbon radical and diradical is the same as or different from another hydrocarbon radical and diradical, respectively, and independently is unsubstituted or substituted by one or more $R^S$.

Preferably, a $(C_1-C_{40})$hydrocarbyl independently is an unsubstituted or substituted $(C_1-C_{40})$alkyl, $(C_3-C_{40})$cycloalkyl, $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, each of the aforementioned groups independently has a maximum of 20 carbon atoms (e.g., $(C_1-C_{20})$alkyl, $(C_3-C_{20})$cycloalkyl, $(C_3-C_{10})$cycloalkyl-$(C_1-C_{10})$alkylene, $(C_6-C_{20})$aryl, or $(C_6-C_{10})$aryl-$(C_1-C_{10})$alkylene), still more preferably 10 carbon atoms (e.g., $(C_1-C_{10})$alkyl, $(C_3-C_{10})$cycloalkyl, $(C_3-C_6)$cycloalkyl-$(C_1-C_4)$alkylene, $(C_6-C_{10})$aryl, or $(C_6-C_{60})$aryl-$(C_1-C_4)$alkylene).

The term "$(C_1-C_{40})$alkyl" means a saturated straight or branched hydrocarbon radical of from 1 to 40 carbon atoms that is unsubstituted or substituted by one or more $R^S$. Preferably, $(C_1-C_{40})$alkyl has a maximum of 20 carbon atoms, more preferably 10 carbon atoms, still more preferably 6 carbon atoms. Examples of unsubstituted $(C_1-C_{40})$alkyl are unsubstituted $(C_1-C_{20})$alkyl; unsubstituted $(C_1-C_{10})$alkyl; unsubstituted $(C_1-C_5)$alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1-C_{40})$alkyl are substituted $(C_1-C_{20})$alkyl, substituted $(C_1-C_{10})$alkyl, trifluoromethyl, and $(C_{45})$alkyl. Preferably, each $(C_1-C_5)$alkyl independently is methyl, trifluoromethyl, ethyl, 1-propyl, or 2-methylethyl.

The term "$(C_6-C_{40})$aryl" means an unsubstituted or substituted (by one or more $R^S$) mono-, bi- or tricyclic aromatic hydrocarbon radical of from 6 to 40 total carbon atoms, of which at least from 6 to 14 are ring carbon atoms, and the mono-, bi- or tricyclic radical comprises 1, 2 or 3 rings, wherein the 2 or 3 rings independently are fused or non-fused and the 1 ring is aromatic and at least of the 2 or 3 rings is aromatic. Preferably, $(C_6-C_{40})$aryl has a maximum of 18 carbon atoms, more preferably 10 carbon atoms, still more preferably 6 carbon atoms. Examples of unsubstituted $(C_6-C_{40})$aryl are unsubstituted $(C_6-C_{20})$aryl; unsubstituted $(C_6-C_{18})$aryl; 2-$(C_1-C_5)$alkyl-phenyl; 2,4-bis$(C_1-C_5)$alkyl-phenyl; phenyl; fluorenyl; tetrahydrofluorenyl; indacenyl; hexahydroindacenyl; indenyl; dihydroindenyl; naphthyl; tetrahydronaphthyl; and phenanthrene. Examples of substituted $(C_6-C_{40})$aryl are substituted $(C_6-C_{20})$aryl; substituted $(C_6-C_{18})$aryl; 2,4-bis[$(C_{20})$alkyl]-phenyl; polyfluorophenyl; pentafluorophenyl; and fluoren-9-one-1-yl.

The term "$(C_3-C_{40})$cycloalkyl" means a saturated cyclic hydrocarbon radical of from 3 to 40 carbon atoms that is unsubstituted or substituted by one or more $R^S$. Preferably, $(C_3-C_{40})$cycloalkyl has a maximum of 20 carbon atoms, more preferably 10 carbon atoms, still more preferably 6 carbon atoms. Examples of unsubstituted $(C_3-C_{40})$cycloalkyl are unsubstituted $(C_3-C_{20})$cycloalkyl, unsubstituted $(C_3-C_{10})$cycloalkyl, cyclopropyl, cyclobutyl, cyclopentyl, cyclohexyl, cycloheptyl, cyclooctyl, cyclononyl, and cyclodecyl. Examples of substituted $(C_3-C_{40})$cycloalkyl are substituted $(C_3-C_{20})$cycloalkyl, substituted $(C_3-C_{10})$cycloalkyl, cyclopentanon-2-yl, and 1-fluorocyclohexyl.

Thus, $(C_1-C_{40})$hydrocarbylene means an unsubstituted or substituted diradical analog of $(C_6-C_{40})$aryl, $(C_3-C_{40})$cycloalkyl, or $(C_2-C_{40})$alkyl, i.e., $(C_6-C_{40})$arylene, $(C_3-C_{40})$cycloalkylene, and $(C_2-C_{40})$alkylene, respectively. More preferably, each of the aforementioned groups independently has a maximum of 20 carbon atoms (e.g., $(C_6-C_{18})$arylene, $(C_3-C_{20})$cycloalkylene, and $(C_2-C_{20})$alkylene), still more preferably 10 carbon atoms (e.g., $(C_6-C_{10})$arylene, $(C_3-C_{10})$cycloalkylene, and $(C_2-C_{10})$alkylene). In some embodiments, the diradicals are on adjacent carbon atoms (i.e., 1,2-diradicals), or spaced apart by one, two, or more intervening carbon atoms (e.g., respective 1,3-diradicals, 1,4-diradicals, etc.). Preferred is a 1,2-, 1,3-, 1,4-, or alpha,omega-diradical, more preferably a 1,2-diradical.

The term "$(C_1-C_{20})$alkylene" means a saturated straight or branched chain diradical of from 1 to 20 carbon atoms that is unsubstituted or substituted by one or more $R^S$. Preferably, $(C_1-C_{20})$alkylene, together with atoms of formula (I) through which the $(C_1-C_{20})$alkylene is bonded, comprise a 5- or 6-membered ring. Examples of unsubstituted $(C_1-C_{20})$alkylene are unsubstituted $(C_1-C_{10})$alkylene, including unsubstituted 1,2-$(C_1-C_{10})$alkylene; —$CH_2$—, —$CH_2CH_2$—, —$(CH_2)_3$—,

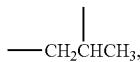

—$(CH_2)_4$—, —$(CH_2)_5$—, —$(CH_2)_6$—, —$(CH_2)_7$—, —$(CH_2)_8$—, and —$(CH_2)_4C(H)(CH_3)$—. Examples of substituted $(C_1-C_{20})$alkylene are substituted $(C_1-C_{10})$alkylene, —$CF_2$—, —$C(O)$—, and —$(CH_2)_{14}C(CH_3)_2(CH_2)_5$— (i.e., a 6,6-dimethyl substituted normal-1,20-eicosylene).

The term "$(C_1-C_{40})$heterohydrocarbyl" means a heterohydrocarbon radical of from 1 to 40 carbon atoms and one or more heteroatoms N (when comprising —N=); O; S; S(O); S(O)$_2$; Si($R^C$)$_3$; P($R^P$); and N($R^N$), wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl. The term "$(C_1-C_{40})$heterohydrocarbylene" means a heterohydrocarbon diradical of from 1 to 40 carbon atoms and one or more heteroatoms Si($R^C$)$_3$, P($R^P$), N($R^N$), N, O, S, S(O), and S(O)$_2$ as defined above. The heterohydrocarbon radical and each of the heterohydrocarbon diradicals independently are on a carbon atom or hetero atom thereof. Each heterohydrocarbon radical and diradical independently is unsubstituted or substituted (by one or more $R^S$), aromatic or non-aromatic, saturated or unsaturated, straight chain or branched chain, cyclic (including mono- and poly-cyclic, fused and non-fused polycyclic) or acyclic, or a combination of two or more thereof; and each heterohydrocarbon is the same as or different from another.

Preferably, a $(C_1-C_{40})$heterohydrocarbyl independently is unsubstituted or substituted $(C_1-C_{40})$heteroalkyl, $(C_2-C_{40})$heterocycloalkyl, $(C_2-C_{40})$heterocycloalkyl-$(C_1-C_{20})$alkylene, $(C_3-C_{40})$cycloalkyl-$(C_1-C_{20})$heteroalkylene, $(C_2-C_{40})$heterocycloalkyl-$(C_1-C_{20})$heteroalkylene, $(C_1-C_{40})$heteroaryl, $(C_1-C_{20})$heteroaryl-$(C_1-C_{20})$alkylene, $(C_6-C_{20})$aryl-$(C_1-C_{20})$heteroalkylene, or $(C_1-C_{20})$heteroaryl-$(C_1-C_{20})$heteroalkylene. More preferably, each of the aforementioned groups has a maximum of 20 carbon atoms, still more preferably 10 carbon atoms. Thus, a more preferred $(C_1-C_{40})$heterohydrocarbyl independently includes unsubstituted or substituted $(C_1-C_{20})$heterohydrocarbyl, e.g., $(C_1-C_{20})$heteroalkyl, $(C_2-C_{20})$heterocycloalkyl, $(C_2-C_{10})$heterocycloalkyl-$(C_1-C_{10})$alkylene, $(C_3-C_{10})$cycloalkyl-$(C_1-C_{10})$heteroalkylene, $(C_2-C_{10})$heterocycloalkyl-$(C_1-C_{10})$heteroalkylene, $(C_1-C_{20})$heteroaryl, $(C_1-C_{10})$heteroaryl-$(C_1-C_{10})$alkylene, $(C_6-C_{10})$aryl-$(C_1-C_{10})$heteroalkylene, or $(C_1-C_{10})$heteroaryl-$(C_1-C_{10})$heteroalkylene. A still more preferred $(C_1-C_{40})$heterohydrocarbyl independently includes unsubstituted or substituted $(C_1-C_{10})$heterohydrocarbyl, e.g., $(C_1-C_{10})$heteroalkyl, $(C_2-C_{10})$heterocycloalkyl, $(C_2-C_6)$heterocycloalkyl-$(C_1-C_4)$alkylene, $(C_3-C_6)$cycloalkyl-$(C_1-C_4)$heteroalkylene, $(C_2-C_6)$heterocycloalkyl-$(C_1-C_4)$heteroalkylene, $(C_1-C_{10})$heteroaryl, $(C_1-C_5)$heteroaryl-$(C_1-C_5)$alkylene, $(C_6)$aryl-$(C_1-C_4)$heteroalkylene, or $(C_1-C_5)$heteroaryl-$(C_1-C_5)$heteroalkylene. Preferably, any $(C_2-C_{18})$heterocycloalkyl independently is unsubstituted or substituted $(C_2-C_9)$heterocycloalkyl.

The aforementioned heteroalkyl and heteroalkylene groups are saturated straight or branched chain radicals or diradicals, respectively, containing $(C_x-C_y)$ carbon atoms and one or more of the heteroatoms Si($R^C$)$_3$, P($R^P$), N($R^N$), N, O, S, S(O), and S(O)$_2$ as defined above, wherein each of the heteroalkyl and heteroalkylene groups independently are unsubstituted or substituted by one or more $R^S$.

Examples of unsubstituted $(C_2-C_{40})$heterocycloalkyl are unsubstituted $(C_2-C_{20})$heterocycloalkyl, unsubstituted $(C_2-C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thia-cyclononyl, and 2-azacyclodecyl.

Examples of unsubstituted $(C_1-C_{40})$heteroaryl are unsubstituted $(C_1-C_{20})$heteroaryl, unsubstituted $(C_1-C_{10})$heteroaryl, pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; tetrazol-5-yl; pyridine-2-yl; pyrimidin-2-yl; pyrazin-2-yl; indol-1-yl; benzimidazole-1-yl; quinolin-2-yl; and isoquinolin-1-yl.

The term "halo" means fluoro (F), chloro (Cl), bromo (Br), or iodo (I) radical. Preferably, halo is fluoro or chloro, more preferably fluoro.

Preferably, there are no O—O, S—S, or O—S bonds, other than O—S bonds in an S(O) or S(O)$_2$ diradical functional group, in the metal complex of formula (I).

Preferably, each substituted (C$_1$-C$_{40}$)hydrocarbyl excludes and is different than unsubstituted or substituted (C$_1$-C$_{40}$)heterohydrocarbyl (i.e., each substituted (C$_1$-C$_{40}$)hydrocarbyl is as defined in the first embodiment, wherein the substituted (C$_1$-C$_{40}$)hydrocarbyl is not an unsubstituted or substituted (C$_1$-C$_{40}$)heterohydrocarbyl); preferably, each substituted (C$_1$-C$_{40}$)hydrocarbylene excludes and is different than unsubstituted or substituted (C$_1$-C$_{40}$)heterohydrocarbylene; and more preferably a combination thereof.

The term "catalytic amount" means a number of moles, or its weight equivalent (e.g., expressed in grams), of a catalyst for catalyzed reaction that is less than a number of moles of a stoichiometric reactant employed in the catalyzed reaction and equal to or greater than a minimum number of moles, or its weight equivalent necessary for at least some product of the catalyzed reaction to be formed and detected (e.g., by mass spectrometry). The number of moles of the catalytic amount may be expressed as a mole percent (mol %) of the number of moles of the stoichiometric reactant. The minimum catalytic amount expressed as a mole percent preferably is 0.001 mole percent. Preferably, the catalytic amount of the isomerization/hydroalumination catalyst of formula (I) is from 0.01 mol % to 50 mol % of the moles of the precursor trialkyl aluminum of formula (A) or olefin (i.e., internal olefin of formula (B) or alpha-olefin of formula (E)), whichever is lower. Typically, the moles of (A) is lower than moles of (B) or (E) and thus the catalytic amount of isomerization/hydroalumination catalyst of formula (I) is equal to [100 times (moles of isomerization/hydroalumination catalyst of formula (I))] divided by (moles of the precursor trialkyl aluminum of formula (A)). More preferably, the catalytic amount of the isomerization/hydroalumination catalyst of formula (I) is at least 0.05 mol %, and still more preferably at least 0.1 mol %. Also more preferably, the catalytic amount of the isomerization/hydroalumination catalyst of formula (I) is 40 mol % or less, and still more preferably 35 mol % or less.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents R$^S$, one or more double and/or triple bonds optionally may or may not be present in substituents R$^S$. The term "unsaturated" means containing one or more carbon-carbon double bonds, carbon-carbon triple bonds, and (in heteroatom-containing groups) carbon-nitrogen, carbon-phosphorous, and carbon-silicon double bonds, not including any such double bonds that may be present in substituents R$^S$, if any, or in (hetero)aromatic rings, if any.

Some embodiments contemplate a trivalent or tetravalent analog of a diradical group. As applied to the diradical group, the term "trivalent or tetravalent analog" respectively means a triradical or tetraradical that is formally derived by abstracting one or two hydrogen atoms, respectively, from the diradical group. Preferably, each abstracted hydrogen atom independently is taken from a C—H functionality. A trivalent analog is preferred over a tetravalent analog.

The term "solvent" means a liquid, preferably aprotic, that is chemically compatible with (i.e., allows) an invention process. Suitable solvents include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; ISOPAR™ hydrocarbons (Exxon Mobil Corporation, Irving, Tex., USA; e.g., ISOPAR™ E); benzene and (C$_1$-C$_5$)alkyl-substituted benzenes such as toluene and xylene; (C$_1$-C$_5$)alkyl-O—(C$_1$-C$_5$)alkyl; (C$_4$-C$_5$)heterocycloalkyl such as tetrahydrofuran, tetrahydropyran, and 1,4-dioxane; (C$_1$-C$_5$)alkyl ethers of (poly)alkylene glycols; and mixtures of the foregoing.

The Precursor Trialkyl Aluminum of Formula (A)

Preferably, each R$^A$ independently contains at least 2 carbon atoms and 24 carbon atoms or fewer, more preferably 18 carbon atoms or fewer, and still more preferably 12 carbon atoms or fewer. Also preferably, each R$^A$ contains the same number of carbon atoms as the remaining R$^A$. Examples of even more preferred trialkyl aluminum of formula (A) are the iso-alkyl aluminums: tri(1-methylethyl) aluminum and tri(1-methylpropyl) aluminum, and the normal-alkyl aluminums: triethyl aluminum (i.e., each R$^A$ is ethyl), tripropyl aluminum, tributyl aluminum, tripentyl aluminum, trihexyl aluminum, triheptyl aluminum, trioctyl aluminum, tridecyl aluminum, triundecyl aluminum, tridodecyl aluminum, tritetradecyl aluminum, trihexadecyl aluminum, and trioctadecyl aluminum.

The Trialkyl Aluminum Compound of Formula (D)

Preferably, each R$^D$ independently contains at least 2 carbon atoms and 24 carbon atoms or fewer, more preferably 18 carbon atoms or fewer, and still more preferably 12 carbon atoms or fewer. Also preferably, each R$^D$ contains the same number of carbon atoms as the remaining R$^D$. Examples of even more preferred trialkyl aluminum compounds of formula (D) are the normal-alkyl-containing aluminums (i.e., at least one, preferably at least two, and more preferably each R$^D$ is the normal-alkyl): ethyl-containing aluminum, propyl-containing aluminum, butyl-containing aluminum, pentyl-containing aluminum, hexyl-containing aluminum, heptyl-containing aluminum, octyl-containing aluminum, decyl-containing aluminum, undecyl-containing aluminum, dodecyl-containing aluminum, tetradecyl-containing aluminum, hexadecyl-containing aluminum, and octadecyl-containing aluminum. Thus, for example, the term "octyl containing aluminum" means a normal-trialkyl aluminum compound of formula (D) wherein at least one R$^D$ is 1-octyl.

The Internal Olefin of Formula (B) and the Primary Alkyl Group Derived from the Internal Olefin of Formula (B)

In some embodiments, the internal olefin of formula (B) and the primary alkyl group derived from the internal olefin of formula (B) each independently contain 4 carbon atoms or more, in other embodiments 5 carbon atoms or more, in still other embodiments 6 carbon atoms or more, and in even other embodiments 8 carbon atoms or more. In some embodiments, the internal olefin of formula (B) and the primary alkyl group derived from the internal olefin of formula (B) each independently contain 24 carbon atoms or fewer, in other embodiments 20 carbon atoms or fewer, in still other embodiments 20 carbon atoms or fewer, and in even other embodiments 18 carbon atoms or fewer. In such embodiments, even more preferably the internal olefin of formula (B) and the primary alkyl group derived from the internal olefin of formula (B) each contain the same number of carbon atoms.

Isomerization/Hydroalumination Catalyst of Formula (I)

In some embodiments of the isomerization/hydroalumination catalyst of formula (I), R$^2$, R$^3$, and R$^4$ are each a hydrogen atom or methyl and M, L, R$^1$, R$^5$, and R$^6$ are as defined above for the first embodiment. More preferred is an isomerization/hydroalumination catalyst of formula (I-A):

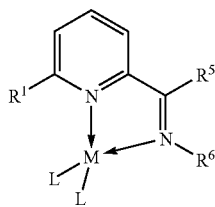

(I-A)

wherein M, L, $R^1$, $R^5$, and $R^6$ are as defined above for the first embodiment.

In some embodiments of the isomerization/hydroalumination catalyst of formula (I), $R^6$ is phenyl and M, L, and $R^1$ to $R^5$ are as defined above for the first embodiment. More preferred more preferred is an isomerization/hydroalumination catalyst of formula (I-B):

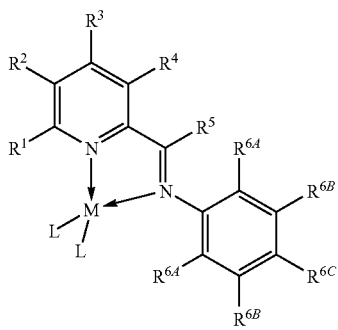

(I-B)

wherein $R^{6C}$ independently is a hydrogen atom or $(C_1$-$C_3)$ alkyl, each of $R^{6A}$ and $R^{6B}$ independently is a hydrogen atom or $(C_1$-$C_3)$alkyl, or $R^{6A}$ and $R^{6B}$ are taken together to form diradical of formula: —C(H)═C(H)—C(H)═C(H)—, and M, L, and $R^1$ to $R^5$ are as defined above for the first embodiment. More preferably, each of $R^{6A}$ independently is hydrogen atom or $(C_1$-$C_3)$alkyl and each of $R^{6B}$ and $R^{6C}$ are hydrogen atoms.

In some embodiments of the isomerization/hydroalumination catalyst of formula (I), $R^1$ is phenyl and M, L, and $R^2$ to $R^6$ are as defined above for the first embodiment. More preferred more preferred is an isomerization/hydroalumination catalyst of formula (I-C):

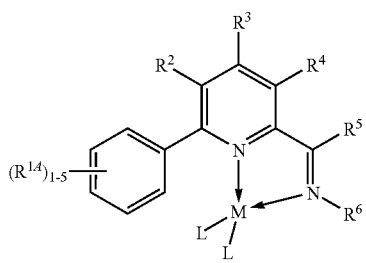

(I-C)

wherein there are from 0 to 5 $R^{1A}$ and each $R^{1A}$ independently is hydrogen atom or $(C_1$-$C_3)$alkyl and M, L, and $R^2$ to $R^6$ are as defined above for the first embodiment.

In some embodiments of the isomerization/hydroalumination catalyst of formula (I), $R^1$ is naphthyl and M, L, and $R^2$ to $R^6$ are as defined above for the first embodiment. More preferred more preferred is an isomerization/hydroalumination catalyst of formula (I-D):

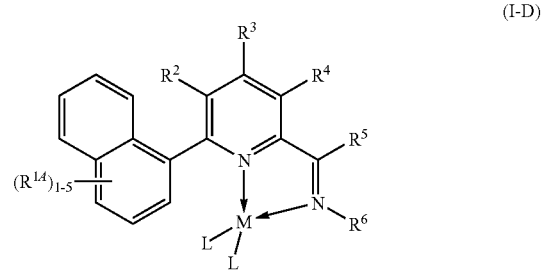

(I-D)

wherein there are from 0 to 5 $R^{1A}$ and each $R^{1A}$ independently is hydrogen atom or $(C_1$-$C_3)$alkyl and M, L, and $R^2$ to $R^6$ are as defined above for the first embodiment. Preferably, $R^6$ is a phenyl substituted with from 1 to 3 $(C_1$-$C_3)$alkyl.

Still more preferred is the isomerization/hydroalumination catalyst of any one of formulas (I-A) to (I-D) wherein M is $Fe^{+2}$. Also still more preferred is the isomerization/hydroalumination catalyst of any one of formulas (I-A), (I-C), and (I-D) wherein $R^6$ is $(C_1$-$C_6)$alkyl or $(C_6$-$C_{10})$aryl, even more preferably phenyl or naphthyl, and yet more preferably phenyl. Also still more preferred is the isomerization/hydroalumination catalyst of formula (I-A) or (I-B) wherein $R^1$ is $(C_1$-$C_6)$alkyl or $(C_6$-$C_{10})$aryl, even more preferably phenyl or naphthyl, and yet more preferably phenyl.

The phenyl and naphthyl in the isomerization/hydroalumination catalysts of formulas (I-A) to (I-D) independently are unsubstituted or substituted with from 1 to 3 substituents $R^S$, wherein $R^S$ is as defined above for the first embodiment. A particularly preferred substituted phenyl is a 2,6-(di$(C_1$-$C_3)$ alkyl)phenyl.

Isomerization/Hydroalumination Catalyst of Formula (I) Having the Formula (II)

In some embodiments of the isomerization/hydroalumination catalyst of formula (II), there are from 1 to 3 $R^{1A}$, and more preferably 2 $R^{1A}$, wherein each $R^{1A}$, L, and $R^2$ to $R^6$ are as defined above for the third embodiment. Still more preferably is an isomerization/hydroalumination catalyst of formula (II-A):

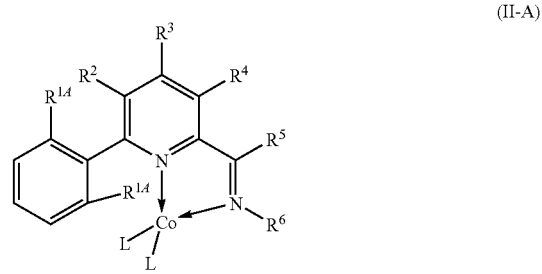

(II-A)

wherein each $R^{1A}$, L, and $R^2$ to $R^6$ is as defined above for the third embodiment. Even more preferably, each $R^{1A}$ independently is $(C_1$-$C_3)$alkyl.

More preferred more preferred is an isomerization/hydroalumination catalyst of formula (II-B):

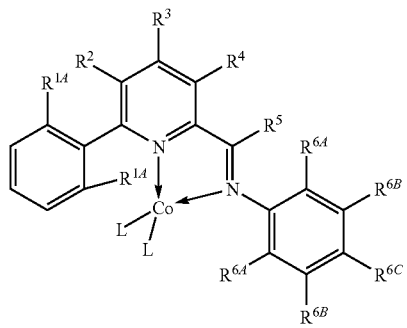

(II-B)

wherein each $R^{1A}$, L, and $R^2$ to $R^5$ are as defined above for the third embodiment, $R^{6C}$ independently is a hydrogen atom or $(C_1-C_3)$alkyl, and each of $R^{6A}$ and $R^{6B}$ independently is a hydrogen atom or $(C_1-C_3)$alkyl. More preferably, each of $R^{6A}$ independently is hydrogen atom or $(C_1-C_3)$alkyl and each of $R^{6B}$ and $R^{6C}$ are hydrogen atoms.

Also more preferred more preferred is an isomerization/hydroalumination catalyst of formula (II-C):

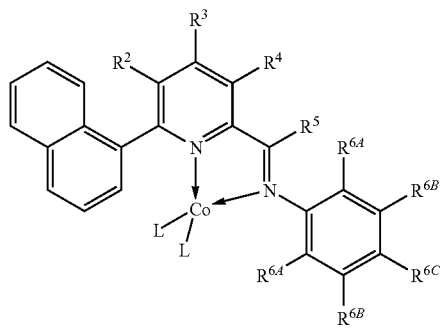

(II-C)

wherein L and $R^2$ to $R^5$ are as defined above for the third embodiment, $R^{6C}$ independently is a hydrogen atom or $(C_1-C_3)$alkyl, and each of $R^{6A}$ and $R^{6B}$ independently is a hydrogen atom or $(C_1-C_3)$alkyl. Still more preferably, $R^{6C}$ is hydrogen atom and each of $R^{6A}$ and $R^{6B}$ independently is a $(C_1-C_3)$ alkyl.

Even more preferred is the isomerization/hydroalumination catalyst of formula (II) of any one of Examples 1 to 5, which are described later.

Also still more preferred is the isomerization/hydroalumination catalyst of any one of formulas (I), (I-A) to (I-D), (II), and (II-A) to (II-C), wherein each L is halo, even more preferably each L is chloro.

Also still more preferred is the isomerization/hydroalumination catalyst of any one of formulas (I), (I-B) to (I-D), (II), and (II-A) to (II-C) wherein each of $R^2$, $R^3$, and $R^4$ independently is a hydrogen atom or methyl, even more preferably hydrogen atom.

Also still more preferred is the isomerization/hydroalumination catalyst of any one of formulas (I), (I-A) to (I-D), (II), and (II-A) to (II-C) wherein $R^5$ is a hydrogen atom, $(C_1-C_6)$ alkyl, or $(C_6-C_{10})$aryl, even more preferably hydrogen atom, methyl, or phenyl, and yet more preferably hydrogen atom or methyl.

In some embodiments the process of the first embodiment employs the isomerization/hydroalumination catalyst of any one of formulas (I-A) to (I-D) and (II-A) to (II-C). The (trialkyl aluminum compound)-forming conditions The (trialkyl aluminum compound)-forming conditions refer to reaction conditions such as solvent(s), atmosphere(s), temperature(s), pressure(s), time(s), and the like that are preferred for giving at least a 10 percent (%) reaction yield of the trialkyl aluminum compound of formula (D) from the process of the first embodiment after 24 hours reaction time. More preferably, the reaction yield is at least 20%, still more preferably at least 50%, and even more preferably at least 70% after 24 hours reaction time.

Preferably, the process of the first embodiment is run under an inert atmosphere (e.g., under an inert gas consisting essentially of, for example, nitrogen gas, argon gas, helium gas, or a mixture of any two or more thereof). Other atmospheres are contemplated, however, and these include sacrificial olefin in the form of a gas.

In some aspects, the process of the first embodiment is run without any solvent, i.e., is a neat process that is run in a neat mixture of the precursor trialkyl aluminum of formula (A), an olefin (e.g., the internal olefin of formula (B), alpha-olefin of formula (E), or the mixture thereof), and the isomerization/hydroalumination catalyst of formula (I). In other aspects, the neat mixture further contains additional ingredients (e.g., catalyst stabilizer such as triphenylphosphine) other than solvent(s). In still other aspects, the process of the first embodiment is run with a solvent or mixture of two or more solvents, i.e., is a solvent-based process that is run as a solvent-containing mixture of the precursor trialkyl aluminum of formula (A), an olefin (e.g., the internal olefin of formula (B), alpha-olefin of formula (E), or the mixture thereof), the isomerization/hydroalumination catalyst of formula (I), and at least one solvent, e.g., an aprotic solvent.

Preferably, the neat process or solvent-based process of the first embodiment is run at a temperature of the neat mixture or solvent-containing mixture of from −20° C. to about 200° C. In some embodiments, the temperature is at least 30° C., and more preferably at least 40° C. In other embodiments, the temperature is 100° C. or lower, more preferably 90° C. or lower, and still more preferably 80° C. or lower. A convenient temperature is about 60° C.

Preferably, the process of the first embodiment is run under a pressure of from about 0.9 atmospheres (atm) to about 10 atm (i.e., from about 91 kiloPascals (kPa) to about 1010 kPa). More preferably, the pressure is about 1 atm (i.e., about 100 kPa).

In some embodiments, the present invention process employs the internal olefin of formula (B) but not the alpha-olefin of formula (E); in other embodiments the present invention process employs the alpha-olefin of formula (E) but not the internal olefin of formula (B); and in still other embodiments the present invention process employs both the at least one alpha-olefin of formula (E) and at least one internal olefin of formula (B), preferably as the aforementioned mixture thereof. In some embodiments, the present invention process employs the isomerization/hydroalumination catalyst of formula (I) as an isomerization catalyst (e.g., when the process of the first embodiment employs the internal olefin of formula (B) but not the alpha-olefin of formula (E) and isomerizes the internal olefin of formula (B) and produces from the resulting trialkyl aluminum compound derived therefrom an alpha-olefin derivative thereof), in other embodiments as a hydroalumination catalyst (e.g., when the process of the first embodiment employs the alpha-olefin of formula (E) but not the internal olefin of formula (B) and hydroaluminates the alpha-olefin of formula (E) to produce a trialkyl aluminum compound derived therefrom), and in still other embodiments as both an isomerization catalyst and hydroalumination catalyst (e.g., when the process of the first embodiment employs the internal olefin of formula (B) but not the alpha-olefin of formula (E) or employs the mixture of at least one alpha-olefin of formula (E) and at least one internal olefin of formula (B)). Mixtures of two or more internal olefins of formula (B); two or more alpha-olefins of formula (E); or any combination of three or more olefins thereof can be employed in the method of the present invention.

In some embodiments, the (trialkyl aluminum compound)-forming conditions prepare the trialkyl aluminum compound of formula (D) by isomerizing the internal olefin of formula (B); hydroaluminating the alpha-olefin of formula (E); or, when ingredient (b) comprises a mixture of the internal olefin of formula (B) and the alpha-olefin of formula (E), both isomerizing the internal olefin of formula (B) and hydroaluminating the alpha-olefin of formula (E).

In some embodiments, the (trialkyl aluminum compound)-forming conditions produce a derivative isomerization/hydroalumination catalyst in situ that is formed from by reaction of the isomerization/hydroalumination catalyst of formula (I) and at least one other ingredient of the process of the first embodiment. The derivative isomerization/hydroalumination catalyst under (trialkyl aluminum compound)-forming conditions gives the trialkyl aluminum compound of formula (D). Such other ingredients include, but are not limited to, (a) the trialkyl aluminum of formula (A), (b) the internal olefin of formula (B), (c) another isomerization/hydroalumination catalyst of formula (I), (d) the trialkyl aluminum compound of formula (D), (e) a co-catalyst (if any), (f) a catalyst stabilizer (if any), (g) a solvent (if any), and a mixture of any two or more thereof.

Converting the Trialkyl Aluminum Compound of Formula (D) to an Alpha-Olefin

In some embodiments, the invention process of the first embodiment further comprises a step of contacting together ingredients comprising ingredients (d), (h), and (i): (d) the trialkyl aluminum compound of formula (D); (h) a catalytic amount of a displacement catalyst; and (i) at least one sacrificial olefin, wherein the contacting of (d), (h), and (i) is performed under (alpha-olefin)-forming conditions and prepares the alpha-olefin of formula (E). The displacement catalyst and the isomerization/hydroalumination catalyst of formula (I) may be the same or, preferably, different.

More preferably, instead the displacement reaction comprises a thermal displacement reaction. The thermal displacement reaction preferably is run conventionally without the displacement catalyst (i.e., without ingredient (h)) and at elevated temperature and elevated pressure and with short residence time (i.e., time of contact) in the presence of excess of a sacrificial 1-olefin to generate the alpha-olefin. A preferred thermal displacement reaction is similar to the thermal displacement reaction described in U.S. Pat. No. 3,391,219 (e.g., see portion of Example 1 at column 7, lines 30-70). Preferably the elevated temperature is at least 140° C., elevated pressure is greater than ambient pressure (i.e., greater than 15 pounds per square inch (psi; 101 kiloPascals (kPa)). For example, the elevated temperature is 280° C. and the elevated pressure is 150 psi (1010 kPa). The residence time is appropriate under the circumstances and readily determined.

In some embodiments, the (alpha-olefin)-forming conditions comprises displacing at least some of the primary alkyl group derived from the internal olefin of formula (B), or derived from the alpha-olefin of formula (E), from the trialkyl aluminum compound of formula (D) and producing therefrom the alpha-olefin of formula (E). The (alpha-olefin)-forming conditions are substantially the same as the (trialkyl aluminum compound)-forming conditions described above. Preferably, the catalytic amount of the displacement catalyst is from 0.01 mol % to 50 mol % of the sacrificial olefin or trialkyl aluminum compound of formula (D), whichever is lower.

The term "displacement catalyst" means any compound, preferably a compound comprising a transition metal M as defined above for the first embodiment, capable of catalyzing displacement of at least one of the $R^D$ that is a primary alkyl group as described above from the trialkyl aluminum compound of formula (D) to yield the alpha-olefin of formula (E). In some embodiments, the displacement catalyst is colloidal Ni, Pt, or Co, nickel acetylacetonate, a cobalt carboxylate (e.g., cobalt 1-naphthenoate or cobalt acetate), nickel bis-1, 5-cyclooctadiene ($Ni(COD)_2$), or a nickel carboxylate (e.g., nickel 1-naphthenoate). The displacement catalyst optionally may be stabilized by combining with a trivalent phosphorous ligand (e.g., triphenylphosphine).

The term "sacrificial olefin" means any alpha-olefin, including the alpha-olefin of formula (E), or a mixture of two or more thereof. Preferably, the sacrificial olefin contains fewer carbon atoms than the carbon atoms contained in the alpha-olefin of formula (E). In some embodiments, the sacrificial olefin contains from 3 to 10 carbon atoms. Examples of preferred sacrificial olefins are propene, 1-butene, and 2-methyl-propene.

Converting the Trialkyl Aluminum Compound of Formula (D) to a Primary Alcohol of Formula (F)

In some embodiments, the invention process of the first embodiment further comprises a step of contacting together ingredients comprising ingredients (d) and (j): (d) the trialkyl aluminum compound of formula (D) and (j) air or another source of oxygen gas, wherein the contacting gives an aluminum alkoxide comprising an alkoxide of at least some of the primary alkyl group derived from the internal olefin of formula (B), or derived from the alpha-olefin of formula (E). A still further contacting step comprising contacting together ingredients comprising ingredients (k) and (l): (k) the aluminum alkoxide and (l) water, gives the primary alcohol of formula (F).

Materials and Methods

General Considerations

Purchase $CoCl_2$ from Aldrich Chemical Company (lot #10820BA). Obtain $FeCl_2$ as anhydrous bead stored in a glove box. Purchase 6-bromo-2-pyridinecarboxaldehyde (CAS Registry Number [34160-40-2]), 2-acetyl-6-bomopyridine (CAS Registry Number [49669-13-8]) aniline, 2,6-dimethylaniline, 2,6-bis(1-methylethyllaniline, n-butanol (anhydrous) and methylene chloride (anhydrous) from Aldrich Chemical Company. Purify hexanes solvent through a column of activated alumina followed by a column of Q5 copper oxide on alumina (Cu-0226 S is obtained from (Engelhard subsidiary of BASF Corporation). Purify tetrahydrofuran (THF) and diethyl ether through columns of activated alumina. Synthesize and store all metal complexes in a Vacuum Atmospheres inert atmosphere glove box under a dry nitrogen atmosphere. Record nuclear magnetic resonance (NMR) spectra on a 300 megahertz (MHz) Varian INOVA spectrometer. Report chemical shifts in parts per million (δ) versus tetramethylsilane and referenced to residual protons in a deuterated solvent.

Determining reaction yield: Add a known amount of heptane as an internal standard to a reaction mixture shortly after adding the reaction ingredients and before heating the reaction mixture. Remove an aliquot from the reaction mixture and place it in a vial. Dilute the aliquot with toluene, then quench the resulting diluted reaction mixture by slowly adding methanol. Filter the resulting quenched mixture through silica gel, eluting with dichloromethane. Analyze the amount of octane in the filtrate by gas chromatography (GC) using an Alltech EC-1 column having a length of 30 meters and GC conditions comprising a temperature of 40° C. and flow rate of 1.0 milliliter per minute (mL/min) The theoretical maximum yield of octane in moles is equal to the lower of the total number of moles of octene(s) used or three times the number of moles of the precursor trialkyl aluminum used. The yield of octane is equivalent to the yield of 1-octylaluminum in a hydroalumination reaction.

Abbreviations (meanings): r.t. (room temperature); g (gram(s)); mL (milliliter(s)); ° C. (degrees Celsius); mmol (millimole(s)); MHz (MegaHertz); Hz (Hertz); and $^1$H-NMR (proton-NMR).

X-Ray Analysis

X-ray analysis is performed as described here.

A red blocks-shaped crystal of dimensions 0.19 millimeters (mm)×0.16 mm×0.15 mm is immersed in oil, Paratone N, Exxon, and mounted on a thin glass fiber. The crystal is transferred to a Bruker SMART PLATFORM diffractometer equipped with a graphite monochromatic crystal, a MoKα radiation source (lambda (λ)=0.71073 angstroms (Å)), and a CCD (charge coupled device) area detector which is kept at 4.930 centimeters (cm) from the crystal. The crystal is bathed in a cold nitrogen stream for the duration of data collection (−100° C.). Three sets of 20 frames each are collected covering three perpendicular sectors of space using the omega (ω) scan method and with a ten second exposure time. Integration of the frames followed by reflection indexing and least squares refinement produces a crystal orientation matrix and a monoclinic lattice.

Data collection is set up to collect a total of 1381 frames in four different runs covering a hemisphere of data. Frame scan parameters are summarized in the following table:

| Run | 2θ | ω | φ | χ | Scan axis | Scan width (°) | Frames (#) | Exposure time (sec.) |
|---|---|---|---|---|---|---|---|---|
| 1 | −28 | −28.00 | 0.00 | 54.70 | 2 | −0.3 | 626 | 30 |
| 2 | −28 | −28.00 | 90.00 | 54.70 | 2 | −0.3 | 455 | 30 |
| 3 | −28 | −28.00 | 180.00 | 54.70 | 2 | −0.3 | 250 | 30 |
| 4 | −28 | −28.00 | 0.00 | 54.70 | 2 | −0.3 | 50 | 30 |

The last run (#4) is the re-measurement of the first 50 frames from run number 1. This is done to monitor crystal and diffractometer stability and to correct for any crystal decay.

Diffractometer setup includes a 0.5 mm monocap collimator providing an X-ray beam of 0.5 mm in diameter. A fine focus X-ray tube with a generator power set at 50 kilovolts (kV) and 35 milliamperes (mA) is used. Program SMART is used for diffractometer control, frame scans, indexing, orientation matrix calculations, least squares refinement of cell parameters, crystal faces measurements and the actual data collection. Program ASTRO is used to set up data collection strategy.

DATA PREPARATION: All 1381 crystallographic raw data frames are read by program SAINT and integrated using 3-dimension (3D) profiling algorithms. The resulting data are reduced to produce hkl reflections and their intensities and estimated standard deviations. The data are corrected for Lorentz and polarization effects. A total of 16990 reflections are collected representing a range of 2.82 to 3.96 redundancy level and have an $R_{sym}$ value range of 2.8%, at the lowest 2θ shell of reflections, to 3.2% at the highest 2θ shell of reflections (55°). Crystal decay correction is applied and is less than 1%. The unit cell parameters are refined by least squares of the setting angles of 8192 reflections. Unit cell parameters are:

a=12.1823(10)Å α=90°.
b=13.9766(11)Å β=110.823(1)°.
c=16.1375(13)Å γ=90°.
V=2568.2(4) cubic angstroms (Å$^3$)

Absorption corrections are applied by integration based on indexed measured faces. Absorption coefficient is 0.814 mm$^{-1}$ and minimum and maximum transmissions are 0.8217 mm$^{-1}$ and 0.914 mm$^{-1}$, respectively.

Data preparation is carried out using program XPREP. A space group is determined to be P2$_1$/c (#14) based on systematic absences. XPREP provides the following crystallographic parameters: 5835 unique reflections ($R_{int}$=3.17%) with indices −11≤h≤15, −18≤k≤16, −20≤l≤20.

The structure is solved by direct methods in SHELXTL6.1 from which the positions of all of the non-H atoms are obtained. The structure is refined, also in SHELXTL6.1, using full-matrix least-squares refinement. The non-H atoms are refined with anisotropic thermal parameters and all of the H atoms are calculated in idealized positions and refined riding on their parent atoms. In the final cycle of refinement, 5294 observed reflections with I>2σ(I) are used to refine 302 parameters and the resulting $R_1$, $wR_2$ and S (goodness of fit) are 3.07%, 7.65% and 1.049, respectively. A correction for secondary extinction is not applied. The maximum and minimum residual electron density peaks in the final Difference Fourier map are 0.319 e. Å$^{-3}$ and −0.307 e. Å$^{-3}$, respectively. The refinement is carried out using F$^2$ rather than F values. $R_1$ is calculated to provide a reference to the conventional R value but its function is not minimized. Additionally, $wR_2$ is the functions that is minimized and not $R_1$.

The linear absorption coefficient, atomic scattering factors and anomalous-dispersion corrections are calculated from values from the International Tables for X-ray Crystallography.

TABLE 1

Crystal data and structure refinement for X.

| | |
|---|---|
| Identification code | X |
| Empirical formula | C28 H28 Cl2 Fe N2 |
| Formula weight | 519.27 |
| Temperature | 173(2) K |
| Wavelength | 0.71073 Å |
| Crystal system | Monoclinic |
| Space group | P2$_1$/c |
| Unit cell dimensions | a = 12.1823(10) Å   α = 90°. |
| | b = 13.9766(11) Å   β = 110.823(1)°. |
| | c = 16.1375(13) Å   γ = 90°. |
| Volume | 2568.2(4) Å$^3$ |
| Z | 4 |
| Density (calculated) | 1.343 Mg/m$^3$ |
| Absorption coefficient | 0.814 mm$^{-1}$ |
| F(000) | 1080 |
| Crystal size | 0.19 × 0.16 × 0.15 mm$^3$ |
| Theta range for data collection | 1.79 to 27.50°. |
| Index ranges | |
| Reflections collected | 16990 |
| Independent reflections | 5835 [R(int) = 0.0317] |
| Completeness to theta = 27.50° | 99.0% |
| Absorption correction | Integration |

TABLE 1-continued

Crystal data and structure refinement for X.

| | |
|---|---|
| Max. and min. transmission | 0.9140 and 0.8217 |
| Refinement method | Full-matrix least-squares on $F^2$ |
| Data/restraints/parameters | 5835/0/302 |
| Goodness-of-fit on $F^2$ | 1.049 |
| Final R indices [I > 2sigma(I)] | R1 = 0.0307, wR2 = 0.0765 [5294] |
| R indices (all data) | R1 = 0.0348, wR2 = 0.0786 |
| Largest diff. peak and hole | 0.319 and −0.307 e · Å$^{-3}$ |

$R1 = \Sigma(||F_o| - |F_c||)/\Sigma|F_o|$
$wR2 = [\Sigma[w(F_o^2 - F_c^2)^2]/\Sigma[w(F_o^2)^2]]^{1/2}$
$S = [\Sigma[w(F_o^2 - F_c^2)^2]/(n-p)]^{1/2}$
$w = 1/[\sigma^2(F_o^2) + (m*p)^2 + n*p]$, $p = [\max(F_o^2, 0) + 2* F_c^2]/3$, m & n are constants.

All thermal ellipsoids described herein are depicted at the 40% probability level.

Preparations

Preparation 1: Preparation of Ligand (1a)

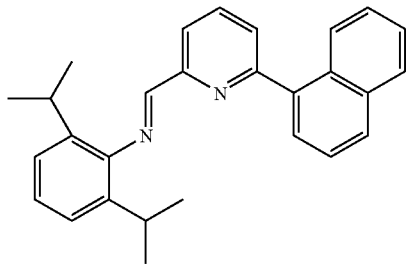

(1a)

Step (a): Preparation of 2-formyl-6-bromopyridine

Fit a 3-neck 500 mL round bottom flask with an additional funnel, mechanical stirrer, and thermocouple well. Dissolve 2,6-dibromopyridine (20 g, 84 millimoles (mmol)) in toluene (150 mL), and place the resulting solution in the addition funnel fitted in a neck of a 3-neck 500 mL round bottom flask. Charge the round bottom flask with toluene (50 mL) and a 1-butyl lithium solution (25 mL, 63 mmol, 2.5 molar (M) in hexane (Acros Organics, Geel, Belgium)). Stir and cool the resulting toluene/1-butyl lithium solution to −10° C. by placing the round bottom flask in a methanol/dry ice bath. Slowly add a 1-butyl magnesium chloride solution (16 mL, 32 mmol, 2.0 M in diethyl ether (Aldrich Chemical Company, Saint Louis, Mo., USA)) via a syringe to the round bottom flask while maintaining the temperature below −5° C. Then stir the resulting toluene/1-butyl lithium/1-butyl magnesium chloride mixture for 0.5 hour at −10 to −5° C. to give a milky white solution. Add dropwise the 2,6-dibromopyridine/toluene solution from the addition funnel over a period of 1 hour while maintaining temperature of the contents in the round bottom flask below −5° C. (mostly −10° C.). Then continue stirring for 1.5 hour to 2 hours while keeping the same bath temperature. Color of the contents in the round bottom flask gradually turns to olive green. Remove an aliquot (about 0.1 mL) and quench it in water (to make 2-bromopyridine from any 6-bromo-pyridyl lithium/magnesium chloride intermediate), then check the resulting quenched material by gas chromatography (GC) to see if there is any remaining 2,6-dibromopyridine. If GC results indicate that all of the 2,6-dibromopyridine has been consumed, add N,N-dimethylformamide (8.5 mL, 0.11 mol, pre-dried over 3A sieves) quickly via syringe to the contents in the round bottom flask. Keep temperature of the bath at −10 to −5° C. Remove an aliquot after 5 minutes, quench it with water, and analyze the resulting quenched material by GC. Observe a sizable 2-formyl-6-bromopyridine peak by GC and, optionally, a barely detectable 2-bromopyridine peak. Quench the reaction by adding aqueous monosodium citrate (slurried/dissolved in 150 mL to 200 mL water; about 1 M) to the contents in the round bottom flask. Vigorously stir the resulting quenched mixture for 10 minutes, and then dilute it with diethyl ether (200 mL). Separate the resulting organic phase from aqueous phase and wash it once with brine (saturated aqueous sodium chloride). Extract the aqueous phase once with diethyl ether, wash the extract once with brine, and combine the extract with the brine-washed original organic phase. Dry the combined diethyl ether mixtures over sodium sulfate ($Na_2SO_4$), and rotary evaporate the solution to give 15 g (theoretical yield is 16 g) of the 2-formyl-6-bromopyridine as a tan solid. Use the 2-formyl-6-bromopyridine without further purification in step (b) below.

Step (b): Preparation of 6-bromo-2-(2,6-diisopropylphenyl)iminopyridine

Prepare a mixture of the 2-formyl-6-bromopyridine (72 g, 0.38 mol) of Step (a) and 2,6-diisopropylaniline (73 g, 0.38 mmol) in 500 mL of anhydrous toluene containing 0.3 nanometer (nm) pore size molecular sieves (6 g) and 80 mg of 4-methylbenzenesulfonic acid (p-TsOH) to give a mixture. Add the mixture to a dry, 500 mL 3-neck round bottom flask equipped with a condenser, an overhead mechanical stirrer, and a thermocouple well. Heat the mixture to 70° C. under a nitrogen gas atmosphere and stir for 12 hours. Cool the mixture to room temperature, filter it, and remove volatiles under reduced pressure until a constant weight to give the 6-bromo-2-(2,6-diisopropylphenyl)iminopyridine as a brown oil. Yield is 0.11 kg (82%). GC/MS 346 (M$^+$), 331, 289, 189, 173, 159, 147, 131, 116, 103, 91, 78. Use the 6-bromo-2-(2,6-diisopropylphenyl)iminopyridine without further purification in step (c) below.

Step (c): Preparation of 6-(1-naphthyl)-2-[(2,6-diisopropylphenyl)imino]pyridine Prepare a mixture by dissolving 1-naphthylboronic acid (55 g, 0.32 mmol) and sodium carbonate ($Na_2CO_3$; 84 g, 0.79 mmol) in 200 mL of degassed 1:1 water/ethanol. Prepare a toluene solution (500 mL) of the 6-bromo-2-(2,6-diisopropylphenyl)-iminopyridine (0.11 g, 0.32 mmol) of step (b) in a 3-neck round bottom flask, and purge the round bottom flask with nitrogen gas. Add the 1-naphthylboronic acid mixture to the toluene solution to give a penultimate mixture. Inside of a dry box, dissolve 1.0 g (0.86 mmol) of tetrakis(triphenylphosphine)palladium(0) in 50 mL of degassed toluene. Remove the resulting degassed toluene solution from the dry box, and add it to the penultimate mixture under nitrogen gas purge. Vigorously stir the resulting biphasic mixture and heat it to 70° C. for from 4 hours to 12 hours. Cool the contents of the round bottom flask to room temperature, separate the organic phase from the aqueous layer, and wash the aqueous layer 3 times with toluene (3×75 mL). Combine the organic phase and the 3 toluene washings, and wash the combined organics 3 times with $H_2O$ (3×200 mL) and dry over magnesium sulfate ($MgSO_4$). Remove the volatiles under reduced pressure, and purify the resulting light yellow oil by recrystallization from methanol to give the 6-(1-naphthyl)-2[(2,6-diisopropylphenyl)imino]pyridine as a yellow solid. Yield 0.11 kg (87%); mp 142-144° C. $^1$H NMR (CDCl$_3$) δ 1.3 (d, 12H), 3.14 (m, 2H), 7.26 (m, 3H), 7.5-7.6 (m, 5H), 7.75-7.8 (m, 3H), 8.02 (m 1H), 8.48 (m, 2H). $^{13}$C NMR (CDCl$_3$) δ 23.96, 28.5, 119.93, 123.50, 124.93, 125.88, 125.94, 126.49, 127.04, 127.24, 128.18, 128.94, 129.7, 131.58, 134.5, 137.56, 137.63, 138.34, 148.93, 154.83, 159.66, 163.86. GC/MS 396 (M$^+$), 380, 351, 337, 220, 207, 189, 147.

Preparation 2: Preparation of Ligand (2a)

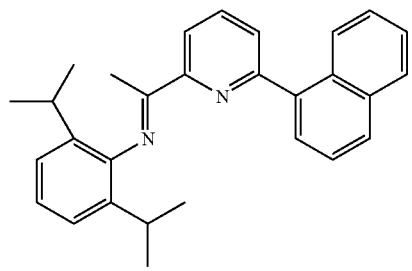

(2a)

Prepare 2-bromo-6-acetylpyridine. Prepare ligand (2a) by repeating the procedure of Preparation 1 except replace N,N-dimethylformamide with N,N-dimethylacetamide to give ligand (2a).

Preparation 3: Preparation of Ligand (3a)

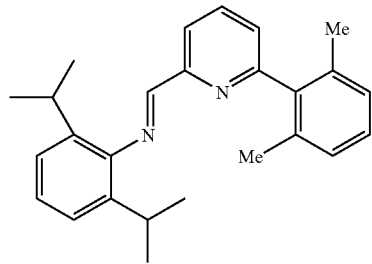

(3a)

Prepare ligand (3a) by repeating the procedure of Preparation 1 except replace 1-naphthylboronic acid with 2,6-dimethylphenylboronic acid to give ligand (3a).

Preparation 4: Preparation of Ligand (4a)

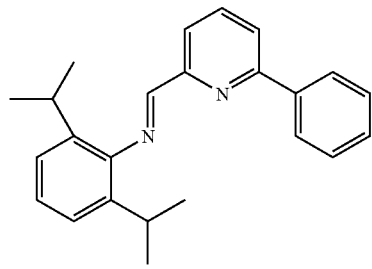

(4a)

Prepare ligand (4a) by repeating the procedure of Preparation 1 except replace 1-naphthylboronic acid with phenylboronic acid (PhB(OH)$_2$) to give ligand (4a).

EXAMPLES OF THE PRESENT INVENTION

Example 1

Preparation of Isomerization/Hydroalumination Catalyst (1)

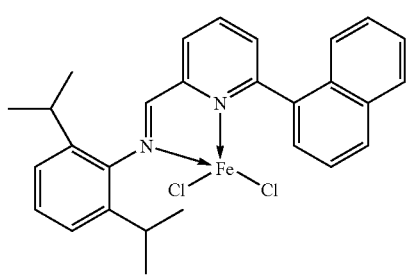

(1)

In a glove box, iron(II) chloride (FeCl$_2$) pellets are weighed in a glass jar and suspended in anhydrous butanol (15 milliliters (mL)). The mixture is stirred vigorously overnight to break up the pellets. The yellow mixture is placed in an aluminum heating block at 80° C. The tan solid ligand (1a) of Preparation 1 is added slowly to the stirring mixture. The mixture becomes red and it is stirred for 15 minutes at 80° C. After cooling to room temperature, a red solid has formed. The mixture is placed in a freezer overnight. The mixture is filtered through a medium glass frit. The bright red solid is rinsed with cold butanol. The filtrate is dark brown. The bright red solid is dried under vacuum for several hours to yield 0.38 g. A $^1$H-NMR is taken in CD$_2$Cl$_2$ (the solid is insoluble in d$_6$-benzene). The color changes to orange in solution. In the glove box, a sample of the red solid is loaded in an NMR tube and a minimum amount of methylene chloride is added (about 0.7 mL). A hexane layer is added on top to fill the tube. The bilayer is placed in the back of the glove box and left undisturbed. X-ray quality crystals of (1) appear in the NMR tube. $^1$H-NMR (CD$_2$Cl$_2$): δ (ppm)=−84.4, −48.6, −16.6, −13.6, −8.5, −0.5, 1.5, 2.3, 3.1, 5.2, 5.5, 6.0, 8.2, 18.8, 50.3, 54.8. The crystals of (1) are subjected to x-ray analysis. FIG. 1 shows Oak Ridge Thermal Ellipsoid Plot (ORTEP) depiction of a single crystal structure derived by the x-ray analysis of isomerization/hydroalumination catalyst (1). As seen in FIG. 1, the isomerization/hydroalumination catalyst (1) has the structure depicted in 2-dimensions above and in 3-dimensions as a tetrahedral iron complex with a single ligand (1a).

Example 2

Preparation of Isomerization/Hydroalumination Catalyst (2)

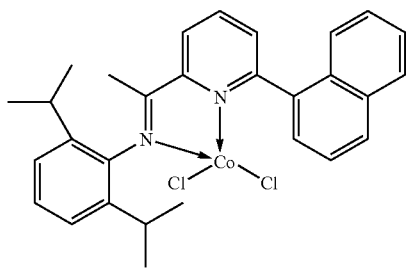
(2)

In a glove box, CoCl$_2$ (0.30 g, 2.3 mmol) is suspended in 1-butanol (15 mL, anhydrous from Aldrich) and stirred for 30 minutes. The mixture is placed in an aluminum heating block at 80° C. and stirred for 30 minutes. The ligand (2a) (0.93 g, 2.3 mmol) of Preparation 2 is added as a solid (slowly) to the stirring solution at 80° C. The mixture turns green and is stirred for 30 minutes. The mixture is cooled to −40° C. and filtered through a glass frit. The green solid is rinsed with cold butanol and diethyl ether. The green solid is dried under vacuum for about 10 minutes and a $^1$H-NMR is taken in CD$_2$Cl$_2$: still appears to be butanol present. The solid is dried under vacuum overnight. $^1$H-NMR indicates the continued presence of butanol. The solid is suspended in 5 mL CH$_2$Cl$_2$. After mixing, approximately 15 mL of hexane is added to the suspension. After mixing, the solid is filtered through a glass frit and dried under vacuum to yield 0.87 g (71% yield) of (2). $^1$H-NMR is taken in CD$_2$Cl$_2$: δ (ppm)=−48.8, −20.1, −13.6, −8.6, −7.3, −4.4, −1.4, 4.2, 5.7, 6.3, 7.0, 8.8, 9.7, 13.7, 41.4, 46.5, 61.3, 63.5.

Example 3

Preparation of Isomerization/Hydroalumination Catalyst (3)

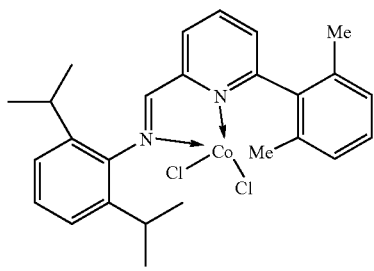
(3)

In the glove box, CoCl$_2$ (0.33 g, 2.5 mmol) is suspended in 1-butanol (15 mL, anhydrous from Aldrich) and stirred for 30 minutes. The mixture is placed in an aluminum heating block at 80° C. and stirred for 30 minutes. The ligand (3a) (0.94 g, 2.5 mmol) of Preparation 3 is added as a solid (slowly) to the stirring solution. The mixture turns green and is stirred for 30 minutes at 80° C. The mixture is cooled to −40° C. and filtered through a glass frit. The resulting green solid is rinsed with cold butanol and diethyl ether. The green solid is dried under vacuum for about 10 minutes and a $^1$H-NMR is taken in CD$_2$Cl$_2$: still appears to be butanol present. The solid is dried under vacuum for about 1 hour. The solid is suspended in 5 mL CH$_2$Cl$_2$. After mixing, approximately 15 mL of hexane is added to the solid. After mixing, the solid is filtered through a glass frit and dried under vacuum to yield 1.03 g (81% yield) of (3). $^1$H-NMR (CD$_2$Cl$_2$): δ (ppm)=−18.9, −15.7, −8.7, −3.7, 1.1, 2.0, 3.4, 3.8, 4.0, 12.9, 51.6, 52.1.

Example 4

Preparation of Isomerization/Hydroalumination Catalyst (4)

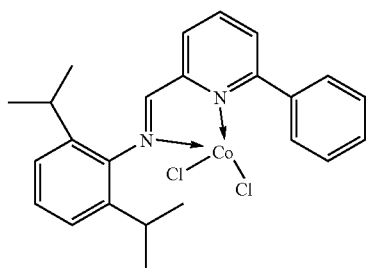
(4)

In the glove box, CoCl$_2$ (0.33 g, 2.5 mmol) is suspended in 1-butanol (15 mL, anhydrous from Aldrich) and stirred for 30 minutes. The mixture is placed in an aluminum heating block at 80° C. and stirred for 30 minutes. The ligand (4a) (0.86 g, 2.5 mmol) of Preparation 4 is added as a solid (slowly) to the stirring solution. The mixture turns dark green and is stirred for 30 minutes at 80° C. The mixture is cooled to −40° C. and filtered through a glass frit. The green solid is rinsed with cold butanol and diethyl ether. The dark green solid is dried under vacuum for about 10 minutes and a $^1$H-NMR is taken in CD$_2$Cl$_2$: still appears to be butanol present. The dark green powder is dried under vacuum for about 1 hour. The solid is suspended in 5 mL CH$_2$Cl$_2$. After mixing, approximately 15 mL of hexane is added to the solid. After mixing, the solid is filtered through a glass frit and dried under vacuum to yield 0.673 g (56% yield) of (4). $^1$H-NMR (CD$_2$Cl$_2$): δ (ppm)=−131, −33.4, −18.2, −12.9, −11.2, −5.5, −0.2, 3.3, 4.6, 5.1, 6.6, 46.1, 58.3.

Example 5

Preparation of Isomerization/Hydroalumination Catalyst (5)

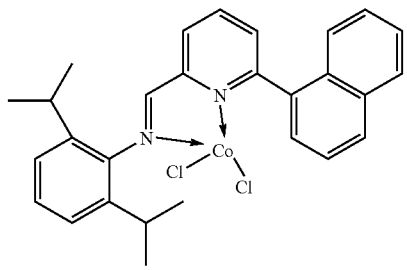
(5)

In the glove box, $CoCl_2$ (0.227 g) is suspended in 1-butanol (15 mL, anhydrous from Aldrich) and stirred for 30 minutes. The mixture is placed in an aluminum heating block at 80° C. and stirred for 30 minutes. The ligand (1a) (0.686 g) of Preparation 1 is added as a solid (slowly) to the stirring mixture. The mixture turned green and is stirred for 30 minutes. The mixture is cooled to −40° C. and filtered through a glass frit. The green solid is rinsed with cold butanol and diethyl ether. After drying under vacuum for about 1 hour, a $^1$H-NMR is taken of the solid: consistent with (5); yield 0.756 g of (5). $^1$H-NMR ($d_6$-benzene): δ (ppm)=−132.4, −49.0, −18.3, −15.3, −13.5, −7.0, −6.3, −2.4, −0.3, 3.0, 4.1, 5.2, 8.9, 10.6, 13.6, 36.2, 49.2, 53.9.

Example 6

Hydroalumination of 1-Octene Catalyzed by Isomerization/Hydroalumination Catalyst (5)

In separate reactions, combine a catalytic amount (1 mol %) of the isomerization/hydroalumination catalyst (5) with toluene and an excess of 1-octene, and then add triisobutylaluminum (0.5 mole equivalents relative to 1-octene). Stir at room temperature. Determine reaction yields as described previously. At 1 mol % catalyst loading, isomerization/hydroalumination catalyst (5) converts 1-octene to an octyl-containing aluminum in up to 73% yield in 2 hours.

Example 7

Isomerization/Hydroalumination of Trans-4-Octene Catalyzed by Isomerization/Hydroalumination Catalyst (5)

Replacing 1-octene with trans-4-octene and repeating the procedure of Example 6 with the isomerization/hydroalumination catalyst (5) provides up to a 7% yield of an octyl-containing aluminum in 14 hours.

Example 8

Isomerization/Hydroalumination of Trans-2-Octene Catalyzed by Isomerization/Hydroalumination Catalyst (5)

Weigh a catalytic amount of the isomerization/hydroalumination catalyst (I/HC) (5) (0.0084 g) into a glass screw-capped vial containing a polytetrafluoroethylene-coated magnetic stir bar and a polytetrafluoroethylene-lined cap. Then add trans-2-octene (1.0 mL) to the vial to form a preliminary mixture. Stir for 2 minutes to 3 minutes, and then add triisobutylaluminum (0.25 mole equivalents relative to octene, approximately 0.32 g) dropwise to the preliminary mixture, which becomes dark colored. Stir the resulting reaction mixture for 45 minutes, and then add 0.25 mL of heptane, which serves as an internal standard. Note that there are no other ingredients in the heptane-containing mixture. Place the heptane-containing mixture in an aluminum heating block and heat it at 60° C. for 18 hours. Cool the heptane-containing mixture, dilute it with toluene (3 mL), and quench it with methanol. Analyze the amount of octane by GC as described previously. The results indicate that the isomerization/hydroalumination catalyst (5) turns over 168 times and the reaction replaces 56% of isobutyl groups in triisobutyl aluminum with 1-octyl groups.

Example 9

Isomerization/Hydroalumination of Trans-2-Octene Catalyzed by Isomerization/Hydroalumination Catalysts (2), (3), (4), or (5)

In separate reactions run in a manner analogous to the procedure of Example 8, combine a catalytic amount (0.25 mol %) of the isomerization/hydroalumination catalyst (I/HC) (2), (3), (4), (5) or a comparator catalyst consisting of $CoCl_2$ with an excess of trans-2-octene (4 mole equivalents relative to triisobutylaluminum), and then add triisobutylaluminum. Heat the resulting reaction mixture at 60° C. At 0.25 mol % catalyst loading, isomerization/hydroalumination catalysts (2), (3), (4), and (5) each converts trans-2-octene to an octyl-containing aluminum. Determine reaction yields after 40 minutes (0.67 hours), 3 hours, and 17 hours of heating time as described previously. The results are shown below in Table 1.

TABLE 1

| | Reaction Yields of octyl-containing aluminum at different reaction times | | | | |
|---|---|---|---|---|---|
| Reaction Time (hours) | Reaction Yield (%) with Comparator $CoCl_2$ | Reaction Yield (%) with I/HC (2) | Reaction Yield (%) with I/HC (3) | Reaction Yield (%) with I/HC (4) | Reaction Yield (%) with I/HC (5) |
| 0.67 | 1.1% | 50 | 42 | 36 | 40 |
| 3 | N.D.[a] | 53 | 49 | N.D. | 47 |
| 17 | 5.7 | 59 | 73 | 75 | 56 |

[a]N.D. means not determined.

As shown by the data in Table 1, the isomerization/hydroalumination catalysts (2) to (5) of Examples (1) to (5) catalyze the preparation of octyl-containing aluminum from trans-2-octene and deliver up to approximately 250 turnovers, wherein turnover means yield of octyl-containing aluminum in millimoles (mmol) divided by catalyst loading in mmol.

Example 10

Isomerization/Hydroalumination of a Mixture of Trans-2-Octene, Trans-3-Octene, and Trans-4-Octene, Catalyzed by Isomerization/Hydroalumination Catalyst (2) or Comparator $Ni(COD)_2$ Catalyst In separate reactions run in a manner analogous to the procedure of Example 8, combine catalytic amounts (0.13 mol %, 0.017 mmol) of the isomerization/hydroalumination catalyst (I/HC) (2) or comparator $Ni(COD)_2$ catalyst with a total of 12.7 millimoles (mmol) of trans-2-octene, trans-3-octene, and trans-4-octene in 2.0 mL of ISOPAR™ E, and then add 4.2 mmol of triisobutylaluminum. Heat the resulting reaction mixture at 60° C. At 0.13 mol % catalyst loading, isomerization/hydroalumination catalyst (2) and comparator $Ni(COD)_2$ catalyst each converts trans-2-octene, trans-3-octene, and trans-4-octene to an octyl-containing aluminum. Determine reaction yields after 30 minutes (0.50 hours), 2 hours, 4 hours, and 19 hours of heating times as described previously. The results are shown below in Table 2.

TABLE 2

Reaction Yields in mmol of octane at different reaction times

| Reaction Time (hours) | Reaction Yield (mmol) with Comparator Ni(COD)$_2$ | Reaction Yield (%) with Comparator Ni(COD)$_2$ | Reaction Yield (mmol) with I/HC (2) | Reaction Yield (%) with I/HC (2) |
|---|---|---|---|---|
| 0.50 | 0.66 mmol | 5.2% | 0.71 | 5.6% |
| 2 | 0.72 mmol | 5.7% | 1.0 | 7.9% |
| 4 | 0.67 mmol | 5.3% | 1.3 | 10% |
| 19 | 0.82 mmol | 6.5% | 2.3 | 18% |

As shown by the results in Table 2, the isomerization/hydroalumination catalyst (2) converted the internal octenes, trans-2-octene, trans-3-octene, and trans-4-octene, to increasing yields of octyl-containing aluminum over time. In contrast, the comparator Ni(COD)$_2$ catalyst does not provide increasing yields of octyl-containing aluminum over time or provides significantly smaller increases compared to the increases with the isomerization/hydroalumination catalyst (2). Thus, the isomerization/hydroalumination catalyst (2) apparently is more stable at 60° C. than is the comparator Ni(COD)$_2$ catalyst. The reaction with the isomerization/hydroalumination catalyst (2) proceeds with greater than 100 turnovers.

Example 11

Isomerization/Hydroalumination of a Mixture of Trans-2-Octene, Trans-3-Octene, and Trans-4-Octene, Catalyzed by Isomerization/Hydroalumination Catalyst (2)

The procedure of Example 10 using the isomerization/hydroalumination catalyst (I/HC) (2) is repeated except the reaction mixture is heated at 80° C. After 15 hours of reaction time, the reaction yield of octane is 1.4 mmol (11% yield).

As shown by the above description, including the Examples, the isomerization/hydroalumination catalyst of formula (I), including the isomerization/hydroalumination catalyst of formula (II), is useful for catalyzing the reaction of the precursor trialkyl aluminum of formula (A) and the internal olefin of formula (B), the alpha-olefin of formula (E), or both to give the trialkyl aluminum compound of formula (D).

While the invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. An isomerization/hydroalumination catalyst of formula (I):

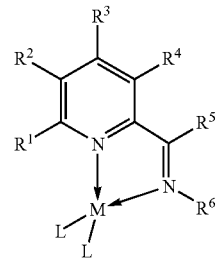

wherein:
Each of $R^1$ and $R^6$ independently is a (C$_1$-C$_{40}$)hydrocarbyl;
Each of $R^2$, $R^3$, $R^4$, and $R^5$ independently is a hydrogen atom or (C$_1$-C$_{40}$)hydrocarbyl;
Each L independently is a halo, hydrogen atom, (C$_1$-C$_{40}$)hydrocarbyl, (C$_1$-C$_{40}$)heterohydrocarbyl, (C$_1$-C$_{40}$)hydrocarbylC(O)N(H)—, (C$_1$-C$_{40}$)hydrocarbylC(O)N((C$_1$-C$_{20}$)hydrocarbyl)-, (C$_1$-C$_{40}$)hydrocarbylC(O)O—, R$^K$R$^L$N—, R$^L$O—, R$^L$S—, or R$^K$R$^L$P—, wherein each R$^K$ and R$^L$ independently is a hydrogen atom, (C$_1$-C$_{40}$)hydrocarbyl, [(C$_1$-C$_{10}$)hydrocarbyl]$_3$Si, [(C$_1$-C$_{10}$)hydrocarbyl]$_3$Si(C$_1$-C$_{10}$)hydrocarbyl, or (C$_1$-C$_{40}$)heterohydrocarbyl, or R$^K$ and R$^L$ are taken together to form a (C$_2$-C$_{40}$)hydrocarbylene or (C$_1$-C$_{40}$)heterohydrocarbylene, wherein each L independently is a monoanionic moiety that is bonded to M; and
Each M independently is a metal, that is nickel, copper, or zinc, the metal being in a formal oxidation state of +2;
Each of the aforementioned (C$_1$-C$_{40}$)alkyl, (C$_1$-C$_{10}$)hydrocarbyl, (C$_1$-C$_{20}$)hydrocarbyl, (C$_1$-C$_{40}$)hydrocarbyl, (C$_1$-C$_{40}$)heterohydrocarbyl, (C$_2$-C$_{40}$)hydrocarbylene, and (C$_1$-C$_{40}$)heterohydrocarbylene independently is the same as or different than another and independently is unsubstituted or substituted with one or more substituents R$^S$; and
Each R$^S$ independently is halo, polyfluoro, perfluoro, unsubstituted (C$_1$-C$_{18}$)hydrocarbyl, F$_3$C—, FCH$_2$O—, F$_2$HCO—, F$_3$CO—, oxo (i.e., =O), R$_3$Si—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, wherein each R independently is an unsubstituted (C$_1$-C$_{18}$)hydrocarbyl.

2. The isomerization/hydroalumination catalyst as in claim 1, wherein the isomerization/hydroalumination catalyst of formula (I) is an isomerization/hydroalumination catalyst of formula (I-A):

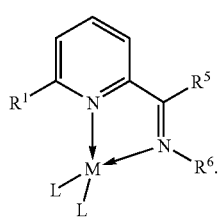

3. The isomerization/hydroalumination catalyst as in claim 1, wherein the isomerization/hydroalumination catalyst of formula (I) is an isomerization/hydroalumination catalyst of formula (I-B):

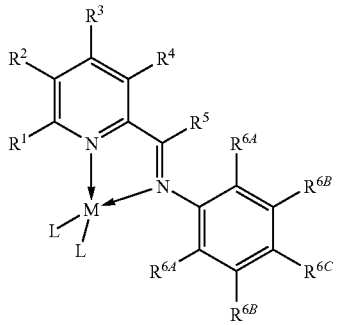

(I-B)

wherein $R^{6C}$ independently is a hydrogen atom or $(C_1-C_3)$ alkyl, and each of $R^{6A}$ and $R^{6B}$ independently is a hydrogen atom or $(C_1-C_3)$alkyl, or $R^{6A}$ and $R^{6B}$ are taken together to form diradical of formula: —C(H)=C(H)—C(H)=C(H)—.

4. The isomerization/hydroalumination catalyst as in claim 1, wherein the isomerization/hydroalumination catalyst of formula (I) is an isomerization/hydroalumination catalyst of formula (I-C):

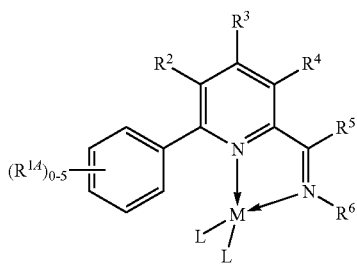

(I-C)

wherein there are from 0 to 5 $R^{1A}$ and each $R^{1A}$ independently is a hydrogen atom or $(C_1-C_3)$alkyl.

5. The isomerization/hydroalumination catalyst as in claim 1, wherein the isomerization/hydroalumination catalyst of formula (I) is an isomerization/hydroalumination catalyst of formula (I-D):

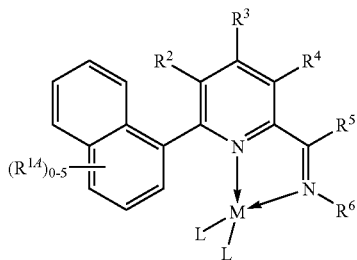

(I-D)

wherein there are from 0 to 5 $R^{1A}$ and each $R^{1A}$ independently is a hydrogen atom or $(C_1-C_3)$alkyl.

6. The isomerization/hydroalumination catalyst as in claim 1, wherein each of $R^2$, $R^3$, and $R^4$ independently is a hydrogen atom or methyl.

7. The isomerization/hydroalumination catalyst as in claim 1, wherein $R^5$ is a hydrogen atom, $(C_1-C_6)$alkyl, or $(C_6-C_{10})$aryl.

8. The isomerization/hydroalumination catalyst as in claim 1, wherein each of $R^1$ and $R^6$ independently is $(C_1-C_6)$alkyl or $(C_6-C_{10})$aryl.

9. An isomer isomerization/hydroalumination catalyst of formula (II):

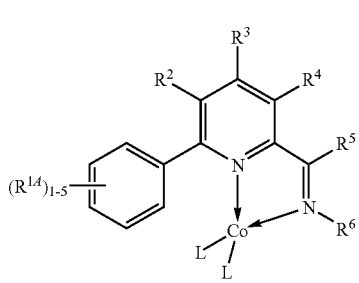

(II)

wherein:

$R^6$ independently is a $(C_1-C_{40})$hydrocarbyl;

Each of $R^2$, $R^3$, $R^4$, and $R^5$ independently is a hydrogen atom or $(C_1-C_{40})$hydrocarbyl;

Each L independently is a halo, hydrogen atom, $(C_1-C_{40})$ hydrocarbyl, $(C_1-C_{40})$heterohydrocarbyl, $(C_1-C_{40})$hydrocarbylC(O)N(H)—, $(C_1-C_{40})$hydrocarbylC(O)N $((C_1-C_{20})$hydrocarbyl)-, $(C_1-C_{40})$hydrocarbylC(O)O—, $R^KR^LN$—, $R^LO$—, $R^LS$—, or $R^KR^LP$—, wherein each $R^K$ and $R^L$ independently is a hydrogen atom, $(C_1-C_{40})$hydrocarbyl, $[(C_1-C_{10})$hydrocarbyl$]_3$Si, $[(C_1-C_{10})$ hydrocarbyl$]_3$Si$(C_1-C_{10})$hydrocarbyl, or $(C_1-C_{40})$heterohydrocarbyl, or $R^K$ and $R^L$ are taken together to form a $(C_2-C_{40})$hydrocarbylene or $(C_1-C_{40})$heterohydrocarbylene, wherein each L independently is a monoanionic moiety that is bonded to M; and Co is cobalt in a formal oxidation state of +2;

Each of the from 1 to 5 $R^{1A}$ independently is a $(C_1-C_{40})$ alkyl that is unsubstituted or substituted with one or more substituents $R^S$ or any two adjacent $R^{1A}$ are taken together to form diradical of formula: —C(H)=C(H)—C(H)=C(H)— and the remainder of $R^{1A}$ are hydrogen atoms;

Each of the aforementioned $(C_1-C_{40})$alkyl, $(C_1-C_{10})$hydrocarbyl, $(C_1-C_{20})$hydrocarbyl, $(C_1-C_{40})$hydrocarbyl, $(C_1-C_{40})$heterohydrocarbyl, $(C_2-C_{40})$hydrocarbylene, and $(C_1-C_{40})$heterohydrocarbylene independently is the same as or different than another and independently is unsubstituted or substituted with one or more substituents $R^S$; and Each $R^S$ independently is halo, polyfluoro, perfluoro, unsubstituted $(C_1-C_{18})$hydrocarbyl, $F_3C$—, $FCH_2O$—, $F_2HCO$—, $F_3CO$—, oxo (i.e., =O), $R_3Si$—, $RO$—, $RS$—, $RS(O)$—, $RS(O)_2$—, $R_2P$—, $R_2N$—, $R_2C$=N—, NC—, $RC(O)O$—, $ROC(O)$—, $RC(O)N(R)$—, or $R_2NC(O)$—, wherein each R independently is an unsubstituted $(C_1-C_{18})$hydrocarbyl.

10. The isomerization/hydroalumination catalyst as in claim 9, wherein the isomerization/hydroalumination catalyst of formula (II) is an isomerization/hydroalumination catalyst of formula (II-A):

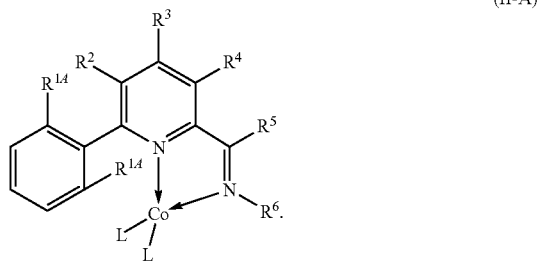

(II-A)

11. The isomerization/hydroalumination catalyst as in claim 1, wherein the isomerization/hydroalumination catalyst of formula (II) is an isomerization/hydroalumination catalyst of formula (II-B):

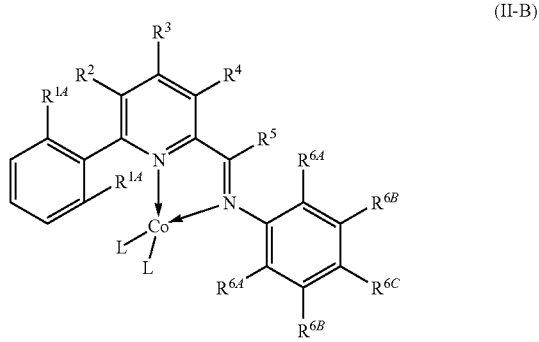

(II-B)

wherein $R^{6C}$ independently is a hydrogen atom or $(C_1$-$C_3)$ alkyl, and each of $R^{6A}$ and
$R^{6B}$ independently is a hydrogen atom or $(C_1$-$C_3)$alkyl.

12. The isomerization/hydroalumination catalyst as in claim 9, wherein the isomerization/hydroalumination catalyst of formula (II) is an isomerization/hydroalumination catalyst of formula (II-C):

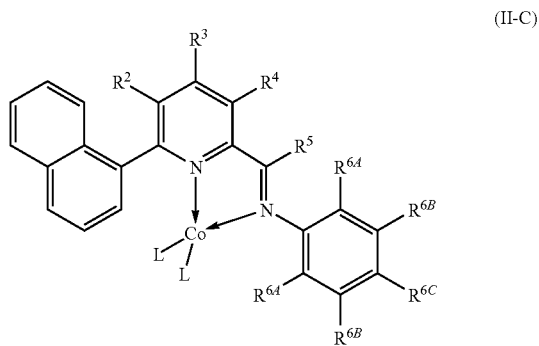

(II-C)

wherein $R^{6C}$ independently is a hydrogen atom or $(C_1$-$C_3)$ alkyl, and each of $R^{6A}$ and
$R^{6B}$ independently is a hydrogen atom or $(C_1$-$C_3)$alkyl.

13. The isomerization/hydroalumination catalyst as in claim 9, wherein each of $R^2$, $R^3$, and $R^4$ independently is a hydrogen atom or methyl.

14. The isomerization/hydroalumination catalyst as in claim 9, wherein $R^5$ is a hydrogen atom, $(C_1$-$C_6)$alkyl, or $(C_6$-$C_{10})$aryl.

15. The isomerization/hydroalumination catalyst as in claim 9, wherein the isomerization/hydroalumination catalyst is any one of formulas (1) to (5):

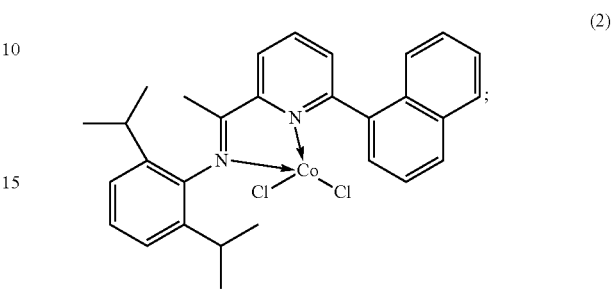

(2)

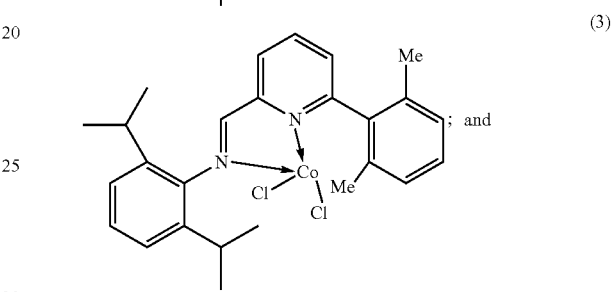

(3)

; and

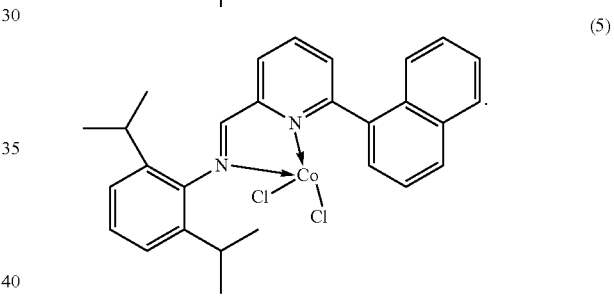

(5)

16. A process for preparing a trialkyl aluminum compound, the process comprising a step of contacting together ingredients comprising ingredients (a), (b), and (c):
(a) a precursor trialkyl aluminum of formula (A):

(A)

wherein of the three $R^A$ in formula (A), two $R^A$ independently are $(C_1$-$C_{40})$alkyl and one $R^A$ independently is $(C_2$-$C_{40})$alkyl;
(b) an internal olefin of formula (B):

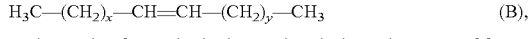

$H_3C$—$(CH_2)_x$—$CH$=$CH$—$(CH_2)_y$—$CH_3$ (B), wherein each of x and y independently is an integer of from 0 to 50, or
an alpha-olefin of formula (E):

$CH_2$=$CH_2$—$(CH_2)_z CH_3$ (E), wherein z is an integer equal to the sum of 1+x+y; or
a mixture comprising the internal olefin of formula (B) and the alpha-olefin of formula (E); and (c) a catalytic amount of an isomerization/hydroalumination catalyst of formula (I):

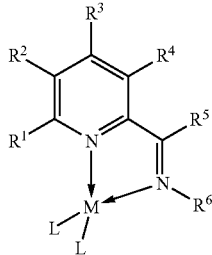

(I)

wherein:
Each of $R^1$ and $R^6$ independently is a $(C_1-C_{40})$hydrocarbyl;
Each of $R^2$, $R^3$, $R^4$, and $R^5$ independently is a hydrogen atom or $(C_1-C_{40})$hydrocarbyl;
Each L independently is a halo, hydrogen atom, $(C_1-C_{40})$hydrocarbyl, $(C_1-C_{40})$heterohydrocarbyl, $(C_1-C_{40})$hydrocarbylC(O)N(H)—, $(C_1-C_{40})$hydrocarbylC(O)N$((C_1-C_{20})$hydrocarbyl)-, $(C_1-C_{40})$hydrocarbylC(O)O—, $R^K R^L N$—, $R^L O$—, $R^L S$—, or $R^K R^L P$—, wherein each $R^K$ and $R^L$ independently is a hydrogen atom, $(C_1-C_{40})$hydrocarbyl, $[(C_1-C_{10})$hydrocarbyl$]_3$Si, $[(C_1-C_{10})$hydrocarbyl$]_3$Si$(C_1-C_{10})$hydrocarbyl, or $(C_1-C_{40})$heterohydrocarbyl, or $R^K$ and $R^L$ are taken together to form a $(C_2-C_{40})$hydrocarbylene or $(C_1-C_{40})$heterohydrocarbylene, wherein each L independently is a monoanionic moiety that is bonded to M; and
Each M independently is a metal that is iron, cobalt, nickel, copper, or zinc, the metal being in a formal oxidation state of +2;

Each of the aforementioned $(C_1-C_{40})$alkyl, $(C_1-C_{10})$hydrocarbyl, $(C_1-C_{20})$hydrocarbyl, $(C_1-C_{40})$hydrocarbyl, $(C_1-C_{40})$heterohydrocarbyl, $(C_2-C_{40})$hydrocarbylene, and $(C_1-C_{40})$heterohydrocarbylene independently is the same as or different than another and independently is unsubstituted or substituted with one or more substituents $R^S$; and
Each $R^S$ independently is halo, polyfluoro, perfluoro, unsubstituted $(C_1-C_{18})$hydrocarbyl, $F_3C$—, $FCH_2O$—, $F_2HCO$—, $F_3CO$—, oxo (i.e., =O), $R_3Si$—, $RO$—, $RS$—, $RS(O)$—, $RS(O)_2$—, $R_2P$—, $R_2N$—, $R_2C$=N—, NC—, $RC(O)O$—, $ROC(O)$—, $RC(O)N(R)$—, or $R_2NC(O)$—, wherein each R independently is an unsubstituted $(C_1-C_{18})$hydrocarbyl;
wherein the contacting step is performed under (trialkyl aluminum compound)-forming conditions and prepares a trialkyl aluminum compound of formula (D):

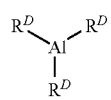

(D)

wherein at least one $R^D$ is a primary alkyl group derived from the internal olefin of formula (B) or derived from the alpha-olefin of formula (E), and any remaining $R^D$ independently are $(C_1-C_{40})$alkyl.

17. The process as in claim 16, wherein each M independently is the metal that is iron, nickel, copper, or zinc.

18. The process as in claim 17, wherein M is iron.

19. The process as in claim 16, wherein M is cobalt.

* * * * *